United States Patent
Hilderbrand et al.

(10) Patent No.: US 8,900,549 B2
(45) Date of Patent: Dec. 2, 2014

(54) COMPOSITIONS AND METHODS FOR DELIVERING A SUBSTANCE TO A BIOLOGICAL TARGET

(75) Inventors: Scott A. Hilderbrand, Swampscott, MA (US); Neal K. Devaraj, Boston, MA (US); Ralph Weissleder, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 251 days.

(21) Appl. No.: 13/126,660

(22) PCT Filed: Nov. 2, 2009

(86) PCT No.: PCT/US2009/062958
§ 371 (c)(1),
(2), (4) Date: Jul. 6, 2011

(87) PCT Pub. No.: WO2010/051530
PCT Pub. Date: May 6, 2010

(65) Prior Publication Data
US 2011/0268654 A1 Nov. 3, 2011

Related U.S. Application Data

(60) Provisional application No. 61/110,121, filed on Oct. 31, 2008.

(51) Int. Cl.
| | | |
|---|---|---|
| A61K 51/00 | (2006.01) |
| A61K 51/04 | (2006.01) |
| B82Y 5/00 | (2011.01) |
| A61K 49/00 | (2006.01) |
| A61K 47/48 | (2006.01) |
| G01N 33/532 | (2006.01) |
| G01N 33/53 | (2006.01) |

(52) U.S. Cl.
CPC ........ *G01N 33/5306* (2013.01); *A61K 51/0474* (2013.01); *B82Y 5/00* (2013.01); *A61K 49/0041* (2013.01); *A61K 49/0019* (2013.01); *A61K 47/4813* (2013.01); *G01N 33/532* (2013.01); *A61K 51/0495* (2013.01); *A61K 47/48746* (2013.01)
USPC ......................................... 424/1.11; 514/183

(58) Field of Classification Search
CPC ............................................... A61K 47/48746
USPC ......................................... 424/1.11; 514/183
See application file for complete search history.

(56) References Cited

U.S. PATENT DOCUMENTS

| | | | |
|---|---|---|---|
| 4,522,811 A | 6/1985 | Eppstein et al. |
| 5,208,020 A | 5/1993 | Chari et al. |
| 5,475,092 A | 12/1995 | Chari et al. |
| 5,585,499 A | 12/1996 | Chari et al. |
| 5,846,545 A | 12/1998 | Chari et al. |
| 6,468,798 B1 | 10/2002 | Debs et al. |
| 6,471,996 B1 | 10/2002 | Sokoll et al. |
| 6,472,375 B1 | 10/2002 | Hoon et al. |
| 7,105,617 B2 * | 9/2006 | Weck et al. ................... 526/171 |
| 2006/0263293 A1 | 11/2006 | Hartmuth et al. |
| 2006/0269942 A1 | 11/2006 | Kolb et al. |
| 2008/0181847 A1 | 7/2008 | Robillard et al. |
| 2009/0062958 A1 | 3/2009 | Morris et al. |

FOREIGN PATENT DOCUMENTS

| | | |
|---|---|---|
| WO | 2007-003054 | 1/2007 |
| WO | 2007/144200 | 12/2007 |
| WO | 2010/051530 | 5/2010 |

OTHER PUBLICATIONS

Devaraj et al (Fast and sensitive pretargeted labeling of cancer cells through a tetrazine/trans-cyclooctene cycloaddition. Angew Chem Int Ed Engl. Sep. 7, 2009;48(38):7013-6).*
Devaraj, N.K. et al "Tetrazine-based cycloadditions: application to pretargeted cell imaging" Bioconjugate Chemistry. Dec. 2008, 19(12), pp. 2297-2299.
Pipkorn, R. et al "Inverse-electron-demand Diels-Alder reaction as a highly efficient chemoselective ligation procedure: Synthesis and function of a bioshuttle for temozolomide transport into prostate cancer cells" Journal of Peptide Science. Mar. 2009. 15, pp. 235-241.
International Search Report and Written Opinion dated Jul. 13, 2010 issued in international application No. PCT/US2009/062958, 11 pgs.
Abbs et al., *Ther. Immunol.* 1(6):325-31; 1994.
Balcar J et al., 1983, *Tet Lett* 24:1481-1484.
Baskin and Bertozzi, 2007, *QSAR Comb. Sci.*, 26, 1211-1219.
Baskin JM et al., 2007, *Proc Natl Acad Sc. USA* 104:16793-16797.
Blackman et al., 2008, *J Am Chem Soc*, 130, 13518-9.
Caron et al., *Mol Ther.* 3(3):310-8; 2001.
Chen et al., 1994, *Bioorg. Med. Chem. Lett.*, 4, 2223-2228.
Colcher et al., *Ann. N.Y. Acad. Sci.* 880:263-80; 1999.
Cole et al., *J Microsc*, 197, 239049; 2000.
Deshayes et al.; *Cell Mol Life Sci.*, 62(16):1839-49; 2005.
Devaraj et al., 2009, *Angew Chem Int Ed Engl*, 48, 7013-6.
Dimandis EP et al. 1991, *Clin Chem* 37:625-637.
El-Andaloussi et al., *Curr Pharm Des.*, 11(28):3597-611; 2005.
Evangelio et al., *Cell Motil Cytoskeleton*; 39, 73-90; 1998.
Farinas and Verkman, *J Biol Chem*, 274, 7603-6; 1999.
Goodpaster and McGuffin; *Anal Chem*, 73, 2004-11; 2001.
Graziano G, 2004, *J Phys Org Chem* 17:100-101.
Guy et al., 1996, *Chem Biol*, 3, 1021-31.
Hangauer and Bertozzi, 2008, *Angew Chem Int Ed Engl*, 47, 2394-7.
Kim et al., *J Am Chem Soc*, 126, 452-3; 2004.
Kwart et al., 1968, *Chem Rev* 68:415-447.
Laughlin et al., 2008, *Science*, 320, 664-7.
Lemieux et al., 2003, *J Am Chem Soc*, 125, 4708-9.
Lewis et al., *Cancer Immunol. Immun.* 37, 255-263; 1993.
Link JA et al., 2003, *Curr Opin Biotechnol* 14:603-609.
Link JA et al., 2003, *J Am Chem Soc* 125:11164-11165.
Manfredi et al., *J Cell Biol*, 94, 688-96; 1982.

(Continued)

*Primary Examiner* — Jake Vu

(74) *Attorney, Agent, or Firm* — Fish & Richardson P.C.

(57) ABSTRACT

The present application provides compositions and methods using bioorthogonal inverse electron demand Diels-Alder cycloaddition reaction for rapid and specific covalent delivery of a "payload" to a ligand bound to a biological target.

2 Claims, 4 Drawing Sheets

(56) References Cited

OTHER PUBLICATIONS

Mellado et al., 1984, *Biochem Biophys Res Commun*, 124, 329-36.
Miller et al., *Nat Protoc*, 1, 824-7; 2006.
Neef and Schultz, 2009, *Angew Chem Int Ed Engl*, 48, 1498-500.
Nicolaou et al., *Angew. Chem. Int. Ed.*, 33, 15-44; 1994.
Ning et al., 2008, *Angewandte Chemie-International Edition*, 47, 2253-2255.
Patelt et al., supra; 2007.
Prescher and Bertozzi, 2005, *Nat Chem Biol*, 1, 13-21.
Prescher JA et al. 2004, *Nature* 430(7002):873-877.
Reiter, *Clin. Cancer Res.* 2:245-52: 1996.
Rideout DC et al., 1980, *J Am Chem Soc* 102:7816-7817.
Ross et al., *Am J Clin Pathol* 119(4):472-485, 2003.
Rostovtsev VV et al., 2002, *Angew Chem Int Ed* 41(14):2596-2599.
Rowinsky et al., *J. Natl. Cancer Inst.*, 82, 1247-1259; 1990.
Royzen, et al., *J. Am Chem. Soc.*; 130, 3760-3761; 2008.
Sauer J et al., 1965, *Chem Ber* 998:1435-1445.
Schiff and Horwitz; *Biochemistry*, 20, 3247-52; 1981.
Shelanski et al., 1973, *Proc Natl Acad Sci U S A*, 70, 765-8; 1973.
Sivakumar et al., 2004, *Org Lett*, 6, 4603-6.
Souto et al., 1995, *Angew. Chem. Int. Ed.*, 34, 2710-2712.
Thalhammer F et al., 1990, *Tet Lett* 47:6851-6854.
Vincenzi et al., *Rev. Oncol. Hematol.* 68:93-106; 2008.
Viht et al., *Bioorg Med Chem Lett*, 13, 3035-9; 2003.
Wang Q et al., 2003, *J Am Chem Soc* 12:3192-3193.
Wu and Senter, *Nat. Biotechnol.* 23:1137-1146; 2005.
Xie and Schultz, *Nat. Rev. Mol. Cell Biol.* 7:775-782; 2006.
Zhou and Fahrni, 2004, *J Am Chem Soc*, 126, 8862-3.
English translation of Office Action issued in Cn200980153250.6 on Apr. 16, 2013 (8 pages).
Jaiswal et al., "Long-term multiple color imaging of live cells using quantum dot bioconjugates," Nature Biotechnology, 21:47-51 (2003).

\* cited by examiner

| Dye | abs(nm) | Em(nm) | quantum yield w/o octene | quantum yield w/ octene | fold increase in fluorescence |
|---|---|---|---|---|---|
| Tetrazine-Coumarin | 430 | 480 | 0.01 | 0.03 | 3.3 |
| Tetrazine-BODIPY FL | 505 | 512 | 0.02 | 0.24 | 15.0 |
| Tetrazine-Oregon Green 488 | 495 | 523 | 0.04 | 0.82 | 18.5 |
| Tetrazine-BODIPY TMR-X | 543 | 573 | 0.02 | 0.40 | 20.6 |
| Tetrazine-VT680 | 669 | 687 | 0.16 | 0.16 | 1.0 |
FIG. 5
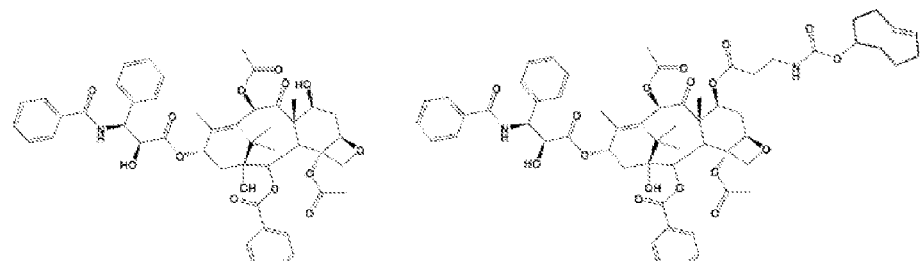
FIG.6A
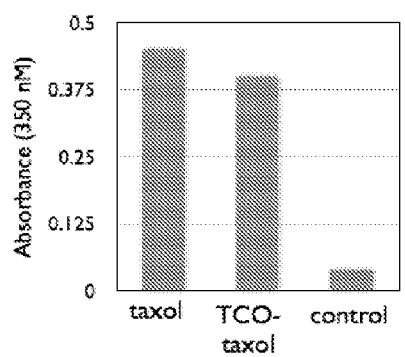
FIG.6B
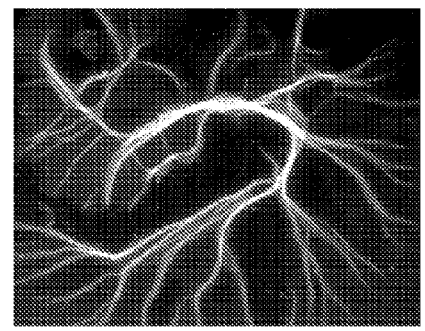
FIG.6C

COMPOSITIONS AND METHODS FOR DELIVERING A SUBSTANCE TO A BIOLOGICAL TARGET

STATEMENT REGARDING FEDERALLY SPONSORED RESEARCH OR DEVELOPMENT

This invention was made with Government support under Grant Nos. NHLBI U01-HL080731 and T32-CA79443 awarded by the National Institutes of Health. The Government has certain rights in the invention.

CLAIM OF PRIORITY

This application is the national stage of International Application Number PCT/US2009/062958, filed on Nov. 2, 2009, which is based on and claims the benefit of U.S. Provisional Patent Application Ser. No. 61/110,121, filed on Oct. 31, 2008, all of which as filed are incorporated herein by reference in their entireties.

FIELD OF THE INVENTION

The present application provides compositions and methods using bioorthogonal inverse electron demand Diels-Alder cycloaddition reactions for rapid and specific covalent delivery of a "payload" to a ligand bound to a biological target.

BACKGROUND OF THE INVENTION

Bioorthogonal reactions for coupling materials in the presence of complex biological milieu are of great interest in biology and medicine. Such reactions have become key components in a variety of applications including protein engineering, immunoassay development, and cell surface modification. (Link J A et al., 2003, Curr Opin Biotechnol 14:603-609; Wang Q et al., 2003, J Am Chem Soc 12:3192-3193; Dimandis E P et al., 1991, Clin Chem 37:625-636; Baskin J M et al., 2007, Proc Natl Acad Sc. USA 104:16793-16797; Link J A et al., 2003, J Am Chem Soc 125:11164-11165). Presently, a few types of bioorthogonal reactions have been reported, the most popular being the Staudinger ligation and the [3+2] cycloaddition "click" reaction between azides and alkynes. (Prescher J A et al., 2004, Nature 430(7002):873-877; Rostovtsev V V et al., 2002, Angew Chem Int Ed 41(14):2596-2599).

Bioorthogonal "click" chemistries are widely used in chemical biology for a myriad of applications such as activity based protein profiling, crosslinking of proteins, monitoring cell proliferation, generation of novel enzyme inhibitors, monitoring the synthesis of newly formed proteins, protein target identification, and studying glycan processing. Perhaps the most fascinating applications involve using these bioorthogonal chemistries to assemble molecules in the presence of living systems such as live cells or even whole organisms (Baskin et al., 2007, Proc Natl Acad Sci USA, 104, 16793-7; Laughlin et al., 2008, Science, 320, 664-7; Prescher and Bertozzi, 2005, Nat Chem Biol, 1, 13-21; Neef and Schultz, 2009, Angew Chem Int Ed Engl, 48, 1498-500; Ning et al., 2008, Angewandte Chemie-International Edition, 47, 2253-2255). These latter applications require that the chemistry be non-toxic and possess kinetics that allow fast reaction to occur with micromolar concentrations of reagents in a time span of minutes to hours.

To fulfill these criteria, various "copper-free" click chemistries have been reported, such as the strain-promoted azide-alkyne cycloaddition and the Staudinger ligation, to react with azides on the surface of live cells both in culture and in in vivo systems such as mice and zebrafish (Prescher and Bertozzi, 2005, Nat Chem Biol, 1, 13-21). However, to date, the application of "click" chemistry in living systems, has been largely limited to extracellular targets and no technique has shown reliable ability to specifically label and image intracellular targets (Baskin and Bertozzi, 2007, QSAR Comb. Sci., 26, 1211-1219). The reasons for this are likely several. In addition to fulfilling the stability, toxicity, and chemoselectivity requirements of "click" chemistry, intracellular live cell labeling requires reagents that can easily pass through biological membranes and kinetics that enable rapid labeling even with the low concentrations of agent that make it across the cell membrane. Additionally, a practical intracellular bioorthogonal coupling scheme would need to incorporate a mechanism by which the fluorescent tag increases in fluorescence upon covalent reaction to avoid visualizing accumulated but unreacted imaging probes (i.e. background). This "turn-on" would significantly increase the signal-to-background ratio, which is particularly relevant to imaging targets inside living cells since a stringent washout of unreacted probe is not possible.

In previous years a number of elegant probes have been introduced whose fluorescence increases after azide-alkyne cycloaddition or staudinger ligation coupling reactions (Sivakumar et al., 2004, Org Lett, 6, 4603-6; Zhou and Fahrni, 2004, J Am Chem Soc, 126, 8862-3; Hangauer and Bertozzi, 2008, Angew Chem Int Ed Engl, 47, 2394-7; Lemieux et al., 2003, J Am Chem Soc, 125, 4708-9). Most of these strategies either require a reactive group intimately attached to the fluorophore thus requiring synthesis of new fluorophore scaffolds or take advantage of a FRET based activation requiring appendage of an additional molecule that can act as an energy transfer agent. Furthermore, most probes utilizing these popular coupling schemes have to date been unable to label intracellular targets in live cells.

The bioorthogonal Diels-Alder reaction is compatible with aqueous environments and has second order rate constants that are known to be enhanced up to several hundred-fold in aqueous media in comparison to organic solvents. (Rideout D C et al., 1980, J Am Chem Soc 102:7816-7817; Graziano G, 2004, J Phys Org Chem 17:100-101). Many Diels-Alder reactions are reversible, therefore, they may not be suitable for biological labeling. (Kwart et al., 1968, Chem Rev 68:415-447), however, the inverse electron demand Diels-Alder cycloaddition of olefins with tetrazines results in irreversible coupling giving dihydropyridazine products (FIG. 2). During this reaction, dinitrogen is released in a retro Diels-Alder step. (Sauer J et al., 1965, Chem Ber 998:1435-1445). A variety of tetrazines and dienophiles including cyclic and linear alkenes or alkynes have been studied in this reaction. Selection of the appropriate reaction partners, allows for tuning of the coupling rate by several orders of magnitude. (Balcar J et al., 1983, Tet Lett 24:1481-1484; Thalhammer F et al., 1990, Tet Lett 47:6851-6854). See also US 2006/0269942, WO 2007/144200, and US 2008/0181847.

SUMMARY OF THE INVENTION

The present invention provides methods and compositions based on a bioorthogonal inverse electron demand Diels-Alder cycloaddition reaction for rapid and specific covalent delivery of a "payload" to a ligand bound to a biological target. The Diels-Alder reaction connects the two components of the reaction, a diene and a dienophile. The diene and dienophile are each physically connected, e.g., through a linker, either to the payload or to a ligand that binds to the target. This bioorthogonal chemistry platform can be used extracellularly or intracellularly, in vivo or in vitro.

Thus, the methods and compositions described herein include using inverse electron demand Diels-Alder cycloaddition chemistry to chemically couple a diene with a dienophile. In some embodiments, the diene is a heteroaromatic ring system containing two adjacent nitrogen atoms. In some embodiments, the diene is a substituted tetrazine. In some embodiments, the diene is a heteroaromatic ring system containing adjacent nitrogen atoms whereby the bioconjugation releases dinitrogen.

In some embodiments, the dienophile is an alkene such as ethylene, propylene or other straight chain alkene. In some embodiments, the dienophile is an internal alkyne, terminal alkyne, or cyclic alkyne such as cyclooctyne. In some embodiments, the alkene is a strained alkene such as norbornene or trans-cyclooctene.

In some embodiments, the invention features a target specific ligand, such as an antibody with a functional group (such as an amine, an alcohol, a carboxylic acid or ester) which can be chemically coupled to a small organic molecule such as trans-cyclooctenol containing a reactive moiety (such as an amine, an alcohol, a carboxylic acid or succinimidyl ester) available for coupling to the antibody, and a dienophile such as an alkene, carbonyl, nitroso, or imine available for reaction with a tetrazine in a Diels-Alder reaction.

Also described herein are methods of labeling and imaging ligands such as small molecules, antibodies and other biomolecules, which are bound to living cells. These methods include the use of an inverse demand Diels-Alder chemistry involving a diene such as a tetrazine or other heteroaromatic ring system possessing at least two nitrogens positioned next to each other and a dienophile such as a strained alkene, norbornene or trans-cyclooctene.

In one aspect, the invention includes compositions for delivering an agent (e.g., a "payload" as described herein, e.g., a detectable agent or therapeutic agent) to a selected biological target. The compositions include a first component attached to a ligand that is specific for the biological target; and a second component attached to the agent, wherein the first and second components are each selected from either a diene or a dienophile and are reactants for the inverse electron demand Diels-Alder reaction. Thus, if the first component is a diene, the second is a dienophile, and vice-versa. As used herein, the term "attached to" includes chemical linkages, e.g., via a reactive group or a linker, as well as incorporation of the diene or dienophile into the ligand or agent, e.g., as a non-natural amino acid or nucleoside.

In embodiments where the agent is a detectable agent, the detectable agent can be selected from the group consisting of organic small molecules, inorganic compounds, nanoparticles, enzymes or enzyme substrates, fluorescent materials, luminescent materials, bioluminescent materials, radioactive materials, and contrast agents. In some embodiments, the detectable agent is linked to a diene, and undergoes fluorogenic activation in the presence of the strained dienophile (i.e., is not fluorescent or weakly fluorescent in the absence of the dienophile, and becomes more strongly fluorescent in the presence of the dienophile upon completion of the Diels-Alder reaction).

In some embodiments where the agent is a therapeutic agent, the therapeutic agent can be, e.g., a small molecule, enzyme inhibitor, receptor protein inhibitor, small interfering RNA (siRNA), cytotoxin, radioactive ion, or other therapeutic agent.

In another aspect, the invention provides methods of delivering a detectable agent to a biological target. The methods include contacting a biological target with a ligand, wherein the ligand is linked to a first component selected from either a diene or a dienophile, to form a ligand-target conjugate; contacting the ligand-target conjugate with a second component that is selected from either a diene or a dienophile and participates in an inverse electron demand Diels-Alder reaction with the first component, and wherein the conjugate is also linked to a detectable agent; under conditions and for a time sufficient time for the first and second components to undergo an inverse electron demand Diels-Alder reaction, thereby delivering the detectable agent to the target. In some embodiments, the detectable agent is selected from the group consisting of organic small molecules, inorganic compounds, nanoparticles, enzymes or enzyme substrates, fluorescent materials, luminescent materials, bioluminescent materials, radioactive materials, and contrast agents.

In some embodiments, the methods further include detecting the detectable agent, e.g., using histochemistry, fluorescence detection, chemiluminescence detection, bioluminescence detection, magnetic resonance imaging, nuclear magnetic resonance imaging, X-ray imaging, X-ray computed tomography, ultrasound imaging, or photoacoustic imaging.

In some embodiments, the biological target is in or on a live or dead cell, tissue section, or organism. In some embodiments, the biological target is in an in vitro assay.

In another aspect the invention features methods for delivering a therapeutic agent to a biological target. The methods include contacting a biological target with a ligand, wherein the ligand is linked to a first component selected from either a diene or a dienophile, to form a ligand-target conjugate; contacting the ligand-target conjugate with a second component that is selected from either a diene or a dienophile and participates in an inverse electron demand Diels-Alder reaction with the first component, and wherein the conjugate is also linked to a therapeutic agent; under conditions and for a time sufficient for the first and second components to undergo an inverse electron demand Diels-Alder reaction, thereby delivering the therapeutic agent to the target. In some embodiments, the therapeutic agent is a small molecule, enzyme inhibitor, receptor protein inhibitor, small interfering RNA (siRNA), cytotoxin, radioactive ion, or other therapeutic agent.

In some embodiments, the cytotoxin is selected from the group consisting of taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, and analogs or homologs thereof.

In some embodiments, the radioactive ion is selected from the group consisting of iodine 125, iodine 131, strontium 89, phosphorous, palladium, cesium, iridium, phosphate, cobalt, yttrium and praseodymium.

In some embodiments, the therapeutic agent is selected from the group consisting of antimetabolites, alkylating agents, anthracyclines, antibiotics, and anti-mitotic agents.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 5 is a table listing the photophysical properties of the dyes before and after reaction.

FIG. 6A shows the structure of Taxol® and the structure of the trans-cyclooctene taxol analog.

FIG. 6B shows the comparison of the ability of taxol, trans-cyclooctene taxol, and a DMSO control to polymerize tubulin in the absence of GTP.

FIG. 6C shows microtubule bundles formed in the presence of trans-cyclooctene taxol treated with tetrazine-BODIPY FL and visualized by fluorescence microscopy.

DETAILED DESCRIPTION

Figure 1:
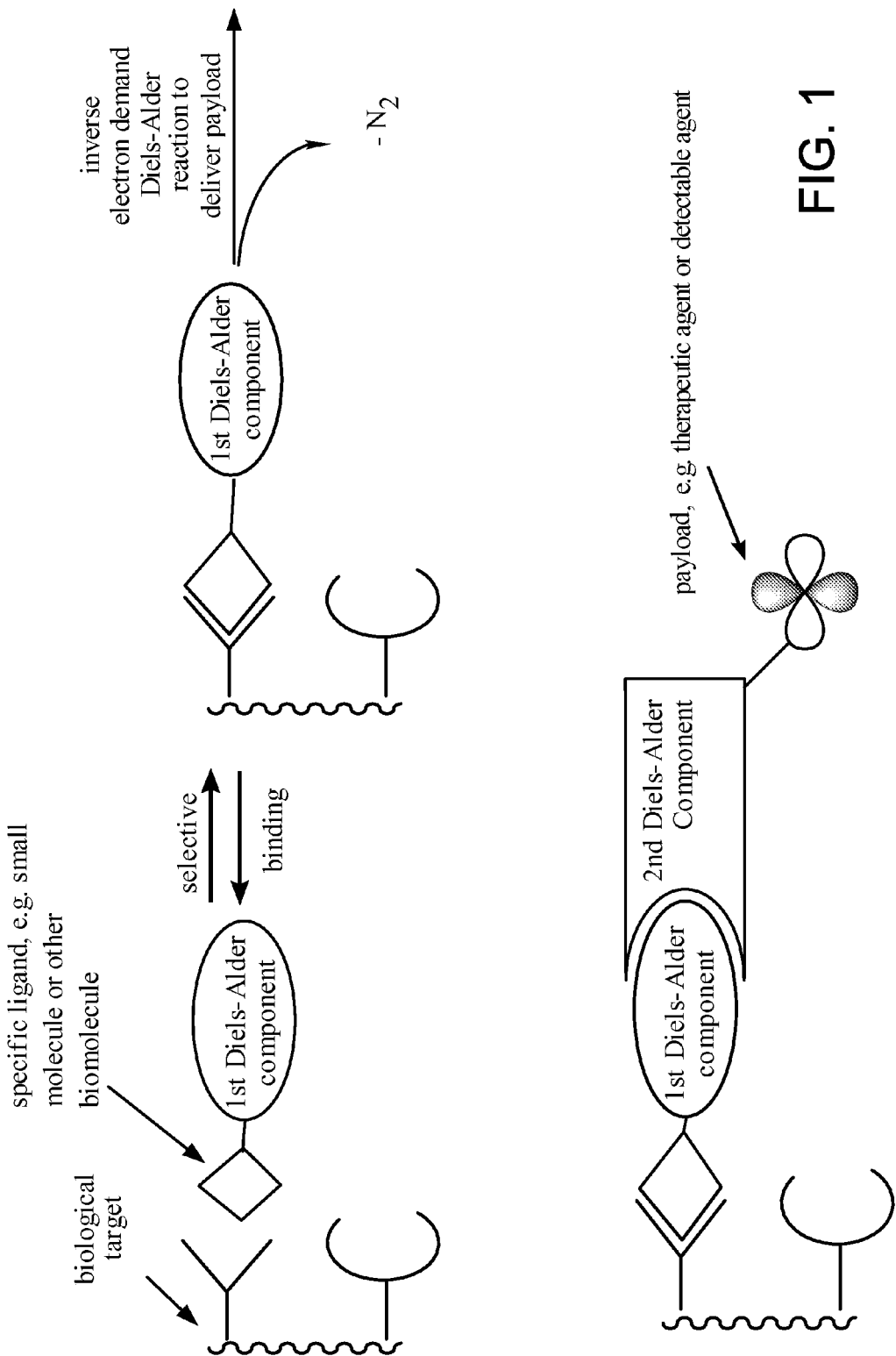
FIG. 1 shows embodiments in which a dienophile is linked to the ligand and a diene is linked to the payload, and an embodiment in which a diene is linked to the ligand and a dienophile is linked to the payload.

The present invention is directed to compositions and methods for delivering a "payload," such as a therapeutic or detectable agent, to a biological target. These methods include the use of bioconjugation using bioorthogonal chemistry such as the inverse electron demand Diels-Alder reaction to deliver a payload, such as a therapeutic or detectable compound, using specific ligands such as antibodies, small molecules and other biomolecules. The specific ligand is attached, optionally through a linker, to one component of the Diels-Alder pair, and the payload is attached, also optionally through a linker, to the other component. For example, if the ligand is attached to a diene, then the payload is attached to a dienophile; if the ligand is attached to the dienophile, then the payload is attached to the diene. The methods and compositions can be used, e.g., in vivo and in vitro, both extracellularly or intracellularly, as well as in assays such as cell free assays.

Targets

The methods and compositions described herein can be used to deliver a payload to any biological target for which a specific ligand exists or can be generated. The ligand can bind to the target either covalently or noncovalently.

Exemplary biological targets include biopolymers, e.g., proteins, nucleic acids, or polysaccharides; exemplary proteins include enzymes, receptors, ion channels, Other exemplary targets include small molecules, e.g., lipids, phospholipids, sugars, peptides, hormones, or neurotransmitters. In some embodiments the target is a tissue- or cell-type specific marker, e.g., a protein that is expressed specifically on a selected tissue or cell type. In some embodiments, the target is a receptor, such as, but not limited to, plasma membrane receptors and nuclear receptors; more specific examples include ligand-gated ion channels, G-protein-coupled receptors, and growth factor receptors. In one embodiment, the receptor is an epidermal growth factor receptor (EGFR).

Ligands

A ligand can be any compound, such as a small molecule or biomolecule (e.g., an antibody or antigen-binding fragment thereof), that binds specifically to a selected target, and can be functionalized by the addition of a diene or dienophile optionally via a linker.

Antibodies

The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments, which retain the ability to bind antigen. Such fragments can be obtained commercially, or using methods known in the art. For example F(ab)2 fragments can be generated by treating the antibody with an enzyme such as pepsin, a non-specific endopeptidase that normally produces one F(ab)2 fragment and numerous small peptides of the Fc portion. The resulting F(ab)2 fragment is composed of two disulfide-connected Fab units. The Fc fragment is extensively degraded and can be separated from the F(ab)2 by dialysis, gel filtration or ion exchange chromatography. F(ab) fragments can be generated using papain, a non-specific thiol-endopeptidase that digests IgG molecules, in the presence of a reducing agent, into three fragments of similar size: two Fab fragments and one Fc fragment. When Fc fragments are of interest, papain is the enzyme of choice because it yields a 50,00 Dalton Fc fragment; to isolate the F(ab) fragments, the Fc fragments can be removed, e.g., by affinity purification using protein A/G. A number of kits are available commercially for generating F(ab) fragments, including the ImmunoPure IgG1 Fab and F(ab')$_2$ Preparation Kit (Pierce Biotechnology, Rockford, Ill.). In addition, commercially available services for generating antigen-binding fragments can be used, e.g., Bio Express, West Lebanon, N.H.

The antibody can be a polyclonal, monoclonal, recombinant, e.g., a chimeric, de-immunized or humanized, fully human, non-human, e.g., murine, or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region.

In addition to utilizing whole antibodies, the invention encompasses the use of binding portions of such antibodies. Such binding portions include Fab fragments, F(ab')2 fragments, and Fv fragments. These antibody fragments can be made by conventional procedures, such as proteolytic fragmentation procedures, as described in J. Goding, *Monoclonal Antibodies: Principles and Practice*, pp. 98-118 (N.Y. Academic Press 1983).

Chimeric, humanized, de-immunized, or completely human antibodies are desirable for applications which include repeated administration, e.g., therapeutic treatment of human subjects.

The antibody can also be a single chain antibody. A single-chain antibody (scFV) can be engineered (see, for example, Colcher et al., Ann. N.Y. Acad. Sci. 880:263-80 (1999); and Reiter, Clin. Cancer Res. 2:245-52 (1996)). The single chain antibody can be dimerized or multimerized to generate multivalent antibodies having specificities for different epitopes of the same target protein. In some embodiments, the antibody is monovalent, e.g., as described in Abbs et al., Ther. Immunol. 1(6):325-31 (1994), incorporated herein by reference.

Methods for making suitable antibodies are known in the art. See, e.g., E. Harlow, et. al., editors, Antibodies: A Laboratory Manual (1988).

In some embodiments, the antibody binds specifically to a tumor antigen, or to an antigen present in a tissue in which a tumor is present. A number of antibodies against cancer-related antigens are known (Ross et al., Am J Clin Pathol 119(4):472-485, 2003). Examples include Alemtuzumab (Campath); Daclizumab (Zenapax); Rituximab (Rituxan); Trastuzumab (Herceptin); Gemtuzumab (Mylotarg); Ibritumomab (Zevalin); Edrecolomab (Panorex); Tositumomab (Bexxar); CeaVac; Epratuzumab (LymphoCide); Mitumomab; Bevacizumab (Avastin); Cetuximab (C-225; Erbitux); Edrecolomab; Lintuzumab (Zamyl); MDX-210; IGN-101; MDX-010; MAb, AME; ABX-EGF; EMD 72 000; Apolizumab; Labetuzumab; ior-t1; MDX-220; MRA; H-11 scFv; Oregovomab; huJ591 MAb, BZL; Visilizumab; TriGem; TriAb; R3; MT-201; G-250, unconjugated; ACA-125; Onyvax-105; CDP-860; BrevaRex MAb; AR54; IMC-1C11; GlioMAb-H; ING-1; Anti-LCG MAbs; MT-103; KSB-303; Therex; KW-2871; Anti-HMI.24; Anti-PTHrP; 2C4 antibody; SGN-30; TRAIL-RI MAb, CAT; H22xKi-4; ABX-MA1; Imuteran; and Monopharm-C. In some embodiments in which the ligand is specific for a tumor antigen or cancerous tissue, the payload can be a therapeutic agent such as a cytotoxin, radioactive agent, or other therapeutic agent useful in treating cancer.

Small Molecules and Biomolecules

Small molecules are low molecular weight organic compounds (less than 2000 Daltons). Small molecules useful in the compositions and methods described herein bind with high affinity to a biopolymer, such as protein, nucleic acid, or polysaccharide, or other biological target. Useful small molecules are capable of being functionalized with a dienophile or a diene. For example, a small molecule can be an agent such as taxol, which binds specifically to microtubules and is capable of being functionalized with a dienophile such as trans-cyclooctene or another alkene. Other examples include small molecules that bind specifically to receptors for hormones, cytokines, chemokines, or other signaling molecules.

Biomolecules are organic molecules produced by living organisms, including large polymeric molecules such as proteins, polysaccharides, and nucleic acids as well as small molecules such as primary metabolites, secondary metabolites, and natural products. Specific small molecule examples include, but are not limited to, estradiol, testosterone, cholesterol, phosphatidylserine, or phosphatidylcholine.

Linker

The term "linker" as used herein refers to a group of atoms, e.g., 0-500 atoms, and may be comprised of the atoms or groups such as, but not limited to, carbon, amino, alkylamino, oxygen, sulfur, sulfoxide, sulfonyl, carbonyl, and imine. The linker chain may also comprise part of a saturated, unsaturated or aromatic ring, including polycyclic and heteroaromatic rings wherein the heteroaromatic ring is an aryl group containing from one to four heteroatoms, N, O or S. Specific examples include, but are not limited to, unsaturated alkanes, polyethylene glycols, and dextran polymers. The linker must not interfere with binding of the ligand to the target, or with the Diels-Alder reaction.

Diels-Alder Pairs

Figure 2:
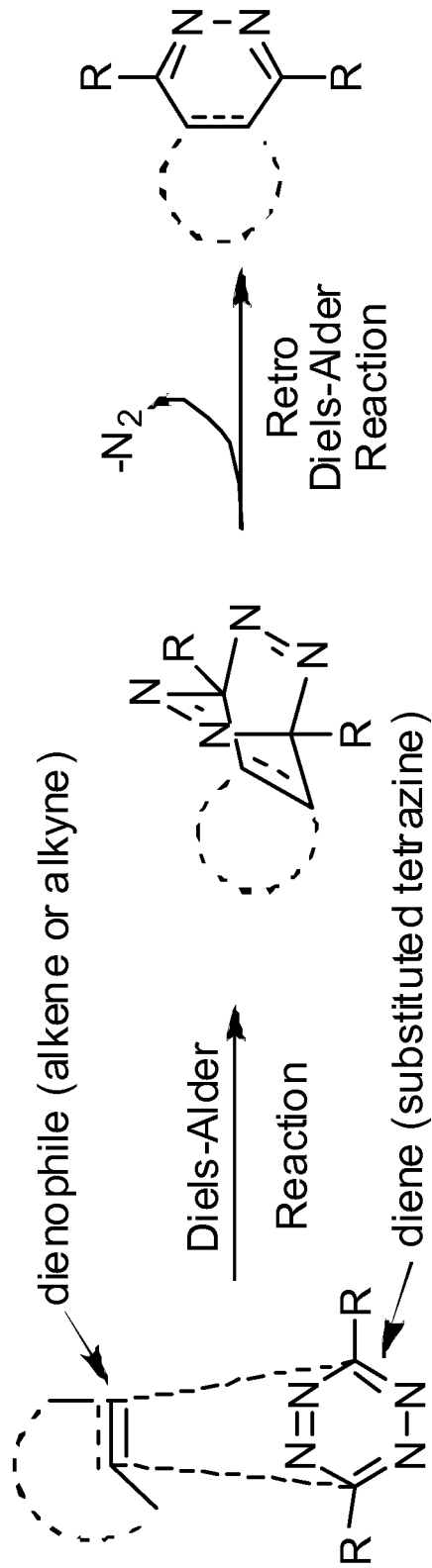
FIG. 2 shows the inverse electron demand Diels-Alder reaction employing a diene (substituted tetrazine) and a dienophile (alkene or alkyne).

The compositions and methods described herein include the use of Diels-Alder pairs that include a diene and a dienophile. The inverse electron demand Diels-Alder cycloaddition reaction of a diene (e.g., a substituted tetrazine) with a dienophile (e.g., an alkene or alkyne), produces an unstable cycloadduct which subsequently undergoes a retro-Diels-Alder cycloaddition reaction to produce dinitrogen as a byproduct and the desired dihydropyrazine (after reaction with an alkene) or pyrazine (after reaction with an alkyne) products (FIG. 2). The dihydropyrazine product may undergo an additional oxidation step to generate the corresponding pyrazine.

Bioorthogonal Chemistry

Bioconjugation methods using inverse electron demand Diels-Alder cycloadditions between tetrazines and highly strained dienophiles such as norbornene and trans-cyclooctene are known in the literature, however the tetrazine used has limited stability to aqueous media. (Blackman et al., 2008, J Am Chem Soc, 130, 13518-9; Devaraj et al., 2009, Angew Chem Int Ed Engl, 48, 7013-6; Devaraj et al., 2008, Bioconjug Chem, 19, 2297-9; Pipkorn et al., 2009, J Pept Sci, 15, 235-41). To improve upon the stability of the tetrazine, a novel asymmetric tetrazine was employed that demonstrated superior stability in water and serum and can react with trans-cyclooctene at rates of approximately $10^3$ $M^{-1}sec^{-1}$ at 37° C. (Devaraj et al., 2009, Angew Chem Int Ed Engl, 48, 7013-6). This extremely fast rate constant allows for the labeling of extracellular targets at low nanomolar concentrations of tetrazine labeling agent, concentrations that are sufficiently low to allow for real-time imaging of probe accumulation.

For example, the bioorthogonal inverse electron demand Diels-Alder reaction can be tailored to provide a straightforward method for the rapid, specific covalent labeling and imaging with ligands such as small molecules and other biomolecules inside living cells. Despite numerous developments in the application of various selective chemistries to extracellular live cell labeling, to date, no method has been universally adapted to intracellular labeling. For example, described herein are a series of "turn-on" tetrazine-linked fluorescent probes that react rapidly via an inverse electron demand Diels-Alder reaction to strained dienophiles such as trans-cyclooctene. Upon cycloaddition, the fluorescence intensity increases dramatically, in some cases by ~20 fold. This fluorescence "turn-on" significantly lowers background signal. These novel probes for live cell imaging of a ligand such as an antibody, small molecule, or other biomolecule modified with a strained alkene can provide a general method for labeling and imaging a ligand bound to a specific target. For example, this bioorthogonal inverse electron demand Diels-Alder reaction can be applied to an asymmetric tetrazine and a strained alkene, which is physically coupled to a small molecule, i.e. a trans-cyclooctene modified taxol analog and can be used to label and image this small molecule bound to intracellular tubules. The rapid reaction rate coupled with fluorescence "turn-on" makes this a nearly ideal method for revealing small molecules inside living cells.

In some embodiments, the ligand, e.g., an antibody, small molecule or other biomolecule, is physically attached to the dienophile (FIG. 1). In some embodiments, the ligand carries a functional group such as an amine, alcohol, carboxylic acid or ester, or other group of atoms on the ligand that can undergo a chemical reaction allowing attachment to the dienophile. Alternatively or in addition, the dienophile or heterodienophile (which can be, e.g., an alkene, alkyne, nitroso, carbonyl or imine) possesses a reactive functional group for attachment to the ligand. Thus, the reactive functional group on the ligand and/or dienophile undergoes a chemical reaction to form a link between the two. In some embodiments, e.g., where the ligand is a biopolymer such as a nucleic acid, peptide, or polypeptide, the functional group on the ligand can be a non-natural nucleoside or amino acid, e.g., as described in Xie and Schultz, Nat. Rev. Mol. Cell Biol. 7:775-782 (2006); for example, the diene or dienophile can be incorporated into a non-natural amino acid as the side chain. One of skill in the art could readily synthesize such compounds. For example, the side chain of phenylalanine or tyrosine could be replace with a diene, e.g., a tetrazine; a dienophile, e.g., a trans-cyclooctene or norbornene, can replace the side chain of phenylalanine, tyrosine, isoleucine, leucine, or tryptophan. These new non-natural amino acids can then be used similarly to known non-natural amino acids, e.g., cells can be incubated in the presence of the new non-natural amino acids, and proteins can be produced that include the diene or dienophile already incorporated into the primary structure of the protein.

In some embodiments, the diene can be a substituted tetrazine or other heteroaromatic ring system with at least two nitrogens adjacent to each other and which is a highly reactive participant in the inverse electron demand Diels-Alder reaction. The diene is linked to the payload (which can be, e.g., a therapeutic agent, fluorescence dye, or other detectable agent) (FIG. 2). In these embodiments, the diene possesses a reactive group such as an amine, alcohol, carboxylic acid or ester, or other group that can undergo a chemical reaction with the reactive moiety on the payload to form a link between the two.

Dienes

Dienes useful in the present disclosure include but are not limited to aromatic ring systems that contain two adjacent nitrogen atoms, for example, tetrazines, pyridazines, substituted or unsubstituted 1,2-diazines. Other 1,2-diazines can include 1,2-diazines annelated to a second π-electron-deficient aromatic ring such as pyrido[3,4-d]pyridazines, pyridazino[4,5-d]pyridazines, and 1,2,4-triazines. Pyridazines can also be fused with a five-membered heterocycle such as imidazo[4,5-d]pyridazines and 1,2,3-triazolo[4,5-d]pyridazines. In some preferred embodiments, the diene is an asymmetrical tetrazine as described herein, e.g., 3-(p-Benzylamino)-1,2,4,5-tetrazine (1).

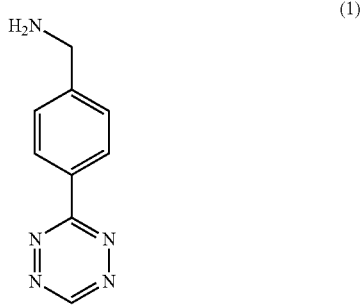 [SMILES: NCc1ccc(-c2nncnn2)cc1]

(1)

Dienophiles

Dienophiles useful in the present methods and compositions include but are not limited to carbon containing dienophiles such as alkenes or alkynes, or compounds containing nitroso, carbonyl or imine groups. In some embodiments, the dienophile is a strained dienophile. As used herein, a "strained" dienophile has a dihedral angle that deviates from the idealized 180 degree dihedral angle. Alternatively, non-strained dienophiles (e.g., styrenes) and/or electron rich electrophiles (e.g., eneamines or vinyl ethers), can also be used with nitroso compounds. Alkenes as used herein refers to an alkyl group having one or more double carbon-carbon bonds such as an ethylene, propylene, and the like. Alkenes can also include cyclic, ring-strained alkenes such as trans-cyclooctene or norbornene carrying a double bond which induces significant ring strain and is thus highly reactive. Alkenes can also include more complex structures such as indoles and azaindoles, electron rich enamines Heterodienophiles containing carbonyl, nitroso or imine groups can also be used. In some preferred embodiments, the dienophile is a trans-cyclooctenol, e.g., (E)-cyclooct-4-enol.

Payload

The methods and compositions described herein are useful for delivering a payload to a biological target. The payload can be used, e.g., for labeling (e.g., a detectable agent such as a fluorophore), or for therapeutic purposes (e.g., a cytotoxin or other therapeutic agent).

Therapeutic Agents

In some embodiments the payload is a therapeutic agent such as a cytotoxin, radioactive ion, or other therapeutic agents. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Radioactive ions include, but are not limited to iodine (e.g., iodine 125 or iodine 131), strontium 89, phosphorous, palladium, cesium, iridium, phosphate, cobalt, yttrium 90, Samarium 153 and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Nucleic acids, e.g., inhibitory nucleic acids, e.g., small interfering RNAs, antisense, aptamers, can also be used as therapeutic agents.

Detectable Agents

Examples of detectable substances include various organic small molecules, inorganic compounds, nanoparticles, enzymes or enzyme substrates, fluorescent materials, luminescent materials, bioluminescent materials, chemiluminescent materials, radioactive materials, and contrast agents. Examples of suitable enzymes include horseradish peroxidase, alkaline phosphatase, beta-galactosidase, or acetylcholinesterase; examples of suitable fluorescent materials include boron-dipyrromethene (BODIPY®), 4,4-difluoro-5,7-dimethyl-4-bora-3a,4a-diaza-s-indacene-3-propionic acid (BODIPY® FL), 6-((4,4-difluoro-1,3-dimethyl-5-(4-methoxyphenyl)-4-bora-3a,4a-diaza-s-indacene-2-propionyl) amino)hexanoic acid, succinimidyl ester (BODIPY® TRM-X), Oregon Green 88, 6-(((4,4-difluoro-5-(2-pyrrolyl)-4-bora-3a,4a-diaza-s-indacene-3-yl)styryloxy)acetyl) aminohexanoic acid, succinimidyl ester (BODIPY® 650/665-X), 7-N,N-diethylaminocoumarin, VIVOTAG 680 (an amine-reactive near-infra-red fluorochrome, from VisEn Medical), umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{18}$F, $^{67}$Ga, $^{81m}$Kr, $^{82}$Rb, $^{111}$In, $^{123}$I, $^{133}$Xe, $^{201}$Tl, $^{125}$I, $^{35}$S, $^{14}$C, or $^{3}$H, $^{99m}$Tc (e.g., as pertechnetate (technetate(VII), TcO$_4^-$) either directly or indirectly, or other radioisotope detectable by direct counting of radioemmission or by scintillation counting. In addition, contrast agents, e.g., contrast agents for MRI or NMR, for X-ray CT, Raman imaging, optical coherence tomogrpahy, absorption imaging, ultrasound imaging, or thermal imaging can be used. Exemplary contrast agents include gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons can also be used.

In some embodiments, the detectable agent is a non-detectable pre-cursor that becomes detectable upon activation. Examples include fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE (VisEn Medical))

When the compounds are enzymatically labeled with, for example, horseradish peroxidase, alkaline phosphatase, or luciferase, the enzymatic label is detected by determination of conversion of an appropriate substrate to product.

In vitro assays in which these compositions can be used include enzyme linked immunosorbent assays (ELISAs), immunoprecipitations, immunofluorescence, enzyme immunoassay (EIA), radioimmunoassay (RIA), and Western blot analysis.

Cell Penetrating Moieties and Agents

In some embodiments the compositions also include a cell penetrating moiety or agent that enhances intracellular delivery of the compositions. For example, the compositions can include a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49. The compositions can also be formulated to include a cell penetrating agent, e.g., liposomes, that enhances delivery of the compositions to the intracellular space.

Uses

The compositions and methods described herein can be used in a number of different scenarios in which delivery of a substance (the "payload") to a biological target is desired, for example delivery of detectable substances for detection of the target, or delivery of a therapeutic agent. Detection methods can include both imaging in vitro and in vivo imaging methods, e.g., immunohistochemistry, bioluminescence imaging (BLI), Magnetic Resonance Imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

As one example, the Diels-Alder coupling reaction as described herein can be used in place of standard avidin (or streptavidin)/biotin coupling procedures. Many tissue types may contain endogenous biotin, so with the current standard biotin-based coupling procedures, an additional step to block the activity of the endogenous biotin may be necessary to eliminate unwanted non-specific background staining. This blocking step is not necessary if the compositions described herein are used.

This procedure is also used for electron microscopy where the fluorophore-dienophile (or -diene) component is replaced by a gold nanoparticle-dienophile (or -diene) conjugate.

The Diels-Alder coupling compositions described herein should also be applicable to any in situ hybridization (ISH) or fluorescence in situ hybridization (FISH) protocol for visualization of DNA or RNA in tissue or cell preparations in which the avidin (streptavidin)/biotin system is employed, e.g., Tyramide Signal Amplification FISH.

The Diels-Alder coupling reaction as described herein can also be used as an alternative to secondary antibodies or in place of standard avidin (or streptavidin)/biotin coupling procedures during a western blot.

In addition, the compositions described herein can be used to deliver therapeutic agents to cells or tissues, e.g., in living animals. Thus a therapeutic compound is attached to one half of the Diels-Alder pair, and a ligand that targets the desired cell or tissue is attached to the other half For example, a ligand such as an antibody that recognizes a tumor cell is attached to one half, and the other half is linked to a payload comprising a cytotoxin, e.g., a toxin or radioactive substance.

These compositions are particularly useful for pretargeting strategies where the ligand has a long half life in the body. For example, monoclonal antibodies have a very long half-life in the blood. This property leads to poor target-to-background ratios when the antibodies are labeled directly with imaging agents or cytotoxins. See, e.g., Wu and Senter, Nat. Biotechnol. 23:1137-1146 (2005). The methods and compositions described herein can circumvent these problems.

Pharmaceutical Compositions and Methods of Administration

The methods described herein include the manufacture and use of pharmaceutical compositions, which include compounds described herein as active ingredients. Also included are the pharmaceutical compositions themselves. In some embodiments, the compositions include a ligand that is specific for a tumor antigen or cancerous tissue, and the payload is a therapeutic agent such as a cytotoxin, radioactive agent, or other therapeutic agent useful in treating cancer.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

All chemicals were purchased from Sigma Aldrich unless noted, and such were used as received. The norbornene, (1S, 2S,4S)-bicyclo[2.2.1]hept-5-en-2-yl acetic acid, was purchased from ChemBridge. All solvents were of reagent grade or higher and were used without further purification. Analytical HPLC and LC/MS were performed on a Waters 2695 HPLC equipped with a 2996 diode array detector, a Micromass ZQ4000 ESI-MS module, and a Grace-Vydac RPC18 column (model 218TP5210) at a flow rate of 0.3 mL/minutes. Preparative HPLC was performed on a Varian ProStar model 210 instrument equipped with a model 335 diode array detector, a model 701 fraction collector, and a Varian RPC18 column (model A6002250X212) at a flow rate of 21 mL/minute.

For all HPLC runs, solvent A comprised water with 0.1% TFA, and solvent B comprised acetonitrile with 10% water and 0.1% TFA. All UV/vis spectra and kinetics experiments were recorded on an Agilent 8453 diode array UV/vis spectrophotometer. Pseudo first order rate constants from all kinetics experiments were calculated using the Agilent UV/vis Chemstation software package Rev. A.10.01. Fluorescence measurements were obtained using a Varian Cary Eclipse fluorescence spectrophotometer. $^1$H (400 MHz) and $^{13}$C NMR (100 MHz) spectra were collected on a Bruker Advance-400 NMR spectrometer at ambient temperature in D$_2$O with 3-(trimethylsilyl)-propionic-2,2,3,3-D$_4$ acid sodium salt (TSP) as an internal standard. High-resolution electrospray ionization (ESI) mass spectra were obtained on a Bruker Daltonics APEX IV 4.7 Tesla Fourier transform mass spectrometer (FT-ICR-MS) in the Department of Chemistry Instrumentation Facility at the Massachusetts Institute of Technology.

Example 1

3-(p-Benzylamino)-tetrazine-VT680 Conjugate (3)

The following example describes an exemplary method of synthesis of 3-(p-benzylamino)-tetrazine-VT680 conjugate.

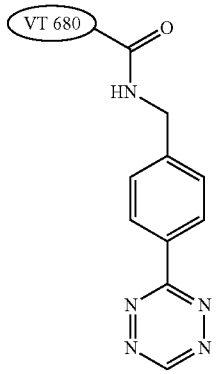 [SMILES: CC(=O)NCc1ccc(-c2nncnn2)cc1]

Step 1. Synthesis of
3-(p-Benzylamino)-1,2,4,5-tetrazine

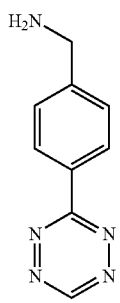

(1)

To a thoroughly blended mixture of 4-(aminomethyl)benzonitrile hydrochloride (25 mmol, 4.21 g), formamidine acetate salt (100 mmol, 10.41 g) and sulfur (25 mmol, 801 mg) was added anhydrous hydrazine (7.84 mL, 250 mmol). After addition of the hydrazine, the reaction mixture became a thick, clear slurry with gas evolution. After stirring vigorously for 20 hours, the now yellow slurry was added to acetic acid (50 mL) and filtered through a glass frit.

Sodium nitrite (125 mmol, 8.63 g) in 15 mL of water was then added to the acetic acid solution, cooled in an ice/water bath, over 15 minutes (Caution: the sodium nitrite addition generates a large amount of toxic nitrogen oxide gasses and should be performed in a well ventilated fume hood). During the sodium nitrite addition, the solution turned bright pink in color. The residue remaining after removal of the acetic acid by rotary evaporation at 60° C. and 5 torr was then washed with acetonitrile (3×20 mL) and filtered.

After removal of the acetonitrile by rotary evaporation, the remaining viscous pink oil (~20 g) was dissolved in 250 mL of buffer A and partially purified in 5 portions by loading onto 70 g Varian Mega Bond Elute RPC18 flash chromatography cartridges eluting with buffer A containing 25% MeOH. The resulting pink fractions were combined, concentrated, and purified by preparative HPLC using a gradient from 0 to 25% buffer B over 30 minutes, giving 1 (0.92 g, 20%) as a pink crystalline solid after solvent removal. The purity of 1 was verified by analytical HPLC. $^1$H NMR (400 MHz, D$_2$O): δ 10.41 (1H, s), 8.52 (2H, d, J=8.4 Hz), 7.73 (2H, d, J=8.4 Hz), 4.34 (2H, s). $^{13}$C NMR (400 MHz, DMSO-d$_6$): δ 169.23, 160.49, 140.57, 135.05, 132.74, 131.91, 45.69. LRMS-ESI [M+H]$^+$ m/z calcd. for [C$_9$H$_{10}$N$_5$]$^+$ 188.0931, found 188.0.

Step 2. Synthesis of
3-(p-Benzylamino)-tetrazine-VT680 Conjugate (3)

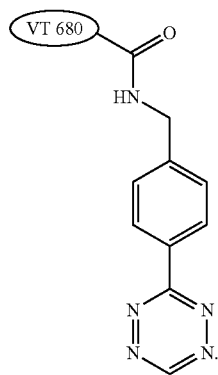

(3)

To a solution of 1 (15.0 mg, 0.08 mmol) in 2.5 mL of 0.1 M PBS, pH 8.3, was added VT680 NHS ester (12.4 mg, 0.01 mmol). The dark blue solution was allowed to stir overnight in the dark. Pure 3 (5.2 mg) was obtained following preparative HPLC of the reaction solution using a gradient from 0 to 25% buffer B over 30 minutes. Product purity was assessed by analytical LC/MS. The synthesis of 3 was confirmed by low resolution ESI mass spectrometry. The expected molecular weight of 3 was calculated to be approximately 1309 for [M+H]$^+$ from the molecular weight of 1 and the vendor supplied molecular weight of 1238 for the NHS ester of VT680 (VivoTag 680 is an amine reactive N-hydroxysuccinimide (NHS) ester of a (benz)indolium-derived far red fluorescent dye). The experimentally observed molecular weight of 3 for [M+H]$^+$ is 1309.7.

Example 2

Synthesis of Additional 3-(p-Benzylamino)-tetrazine-fluorophore Conjugates

General Procedure for the Synthesis of Tetrazine Fluorophore Conjugates.

To a solution of 3-(4-benzylamino)-1,2,4,5-tetrazine (10 μmol) in anhydrous DMF (0.5 mL) was added the succinimidyl ester of the appropriate fluorophore (2.5 μmol) and triethylamine (10 μmol). The resulting solution was allowed to shake overnight in the dark. The crude reaction mixture was then purified by preparative reverse phase HPLC using a gradient from 0 to 100% buffer B. The identity and purity of the conjugates were confirmed by electrospray mass spectrometry and analytical HPLC, respectively. Via this procedure the following conjugates were prepared: tetrazine-BODIPY FL, tetrazine-BODIPY TMR-X, tetrazine-Oregon Green 488, tetrazine-BODIPY 650-665, and tetrazine-coumarin using the succinimidyl esters of BODIPY-FL, BODIPY TMR-X, Oregon Green 488, BODIPY 650-665, and 7-diethylaminocoumarin-3-carboxylic acid, respectively.

Example 3

5-(4-(1,2,4,5-Tetrazin-3-yl)benzylamino)-5-oxopentanoic Acid

The following example describes an exemplary method of synthesis of 5-(4-(1,2,4,5-Tetrazin-3-yl)benzylamino)-5-oxopentanoic acid.

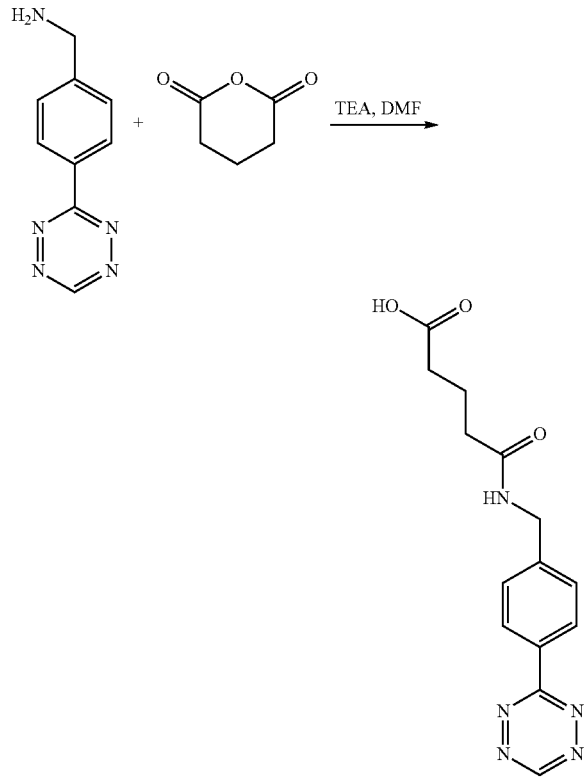

To a solution of 3-(p-benzylamino)-1,2,4,5-tetrazine (9.4 mg, 0.05 mmol) in anhydrous DMF (1.5 mL) was added glutaric anhydride (22.8 mg, 0.2 mmol) and triethylamine (7 μL, 0.05 mmol). The resulting solution was allowed to stir for 3 hours. The crude product was purified by preparative reverse-phase HPLC using a gradient from 0 to 100% buffer B over 30 minutes. After solvent removal, pure 5-(4-(1,2,4,5-tetrazin-3-yl)benzylamino)-5-oxopentanoic acid (9.9 mg, 66%) was isolated as a pink solid. $^1$H NMR (400 MHz, CD$_3$OD): δ 10.31 (1H, s), 8.55 (2H, d, J=6.8 Hz), 7.55 (2H, d, J=6.8 Hz), 4.50 (2H, s), 2.37-2.33 (4H, m), 1.93 (2H, pentet, J=5.8 Hz). LRMS-ESI [M+H]$^+$ m/z calcd. for [C$_{14}$H$_{16}$N$_5$O$_3$]$^+$ 302.12, found 302.2.

Example 4

(4-(1,2,4,5-Tetrazin-3-yl)phenyl)methanol

The following example describes an exemplary method of synthesis of (4-(1,2,4,5-Tetrazin-3-yl)phenyl)methanol.

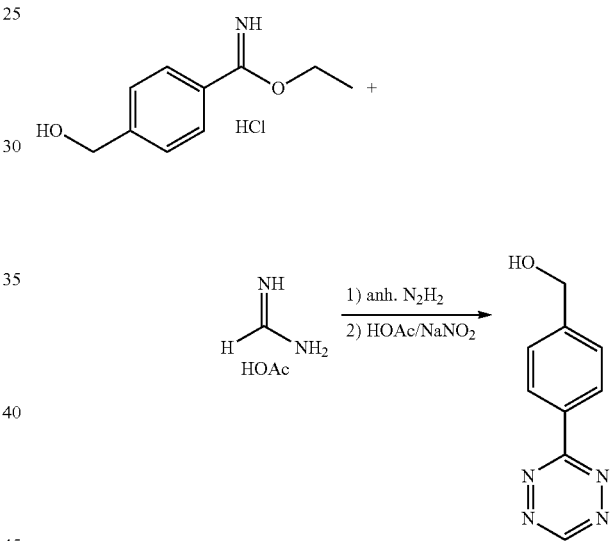

To a mixture of 4-(hydroxymethyl)-benzenecarboximidic acid, ethyl ester, hydrochloride (1 mmol, 216 mg) and formamidine acetate (5 mmol, 521 mg) was added anhydrous hydrazine (20 mmol, 630 uL) the resulting viscous oil was allowed to stir. After 1 hour, acetic acid (3 mL) was added followed by sodium nitrite (690 mg, 10 mmol) as a finely divided powder. The now bright pink solution was allowed to stir for 15 minutes and then diluted with 15 mL of water. The aqueous crude reaction was subsequently extracted with methylene chloride (4×10 mL). The organic extracts were dried with MgSO$_4$. After solvent removal, the crude pink product was purified by flash chromatography (silica gel) first washing with 100% methylene chloride, followed by methylene chloride with 1% methanol, giving (4-(1,2,4,5-tetrazin-3-yl)phenyl)methanol (40 mg, 21%) as a bright pink solid. LRMS-ESI [M+H]$^-$ calcd. for C$_9$H$_9$N$_4$O$^-$: 189.08, found: 188.8.

Example 5

2-(6-Methyl-1,2,4,5-tetrazin-3-yl)ethanol

The following example describes an exemplary method of synthesis of 2-(6-Methyl-1,2,4,5-tetrazin-3-yl)ethanol.

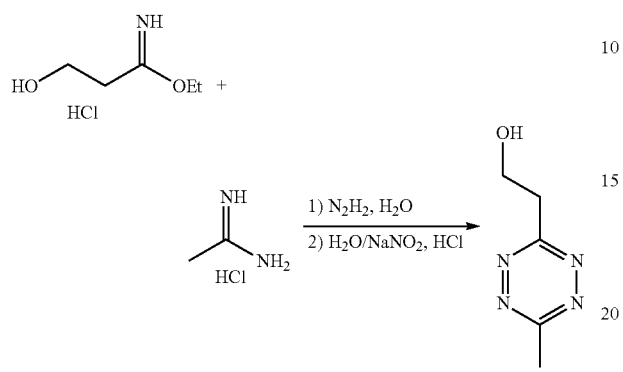

To a mixture of ethyl 3-hydroxypropanimidate hydrochloride (2 mmol, 307 mg) and acetamidine hydrochloride (10 mmol, 945 mg) was added hydrazine hydrate (2 mL) under an atmosphere of argon. After stirring at room temperature for 2 hours, the mixture was diluted with water (25 mL) and sodium nitrite (25 mmol, 1.72 g) was added. To this solution was added 2% aqueous HCl dropwise on an ice bath until the now pink solution reached a pH of 3. The aqueous solution was extracted with methylene chloride (5×50 mL), dried with magnesium sulfate, the solvent was removed by rotary evaporation, and then dried under vacuum to afford the product, 2-(6-methyl-1,2,4,5-tetrazin-3-yl)ethanol (140 mg, 37%), as a pink oil. LRMS-ESI [M+H]$^+$ calcd. for $C_5H_9N_4O^+$: 141.08, found: 140.7.

Example 6

2-(1,2,4,5-Tetrazin-3-yl)ethanol

The following example describes an exemplary method of synthesis of 2-(1,2,4,5-Tetrazin-3-yl)ethanol.

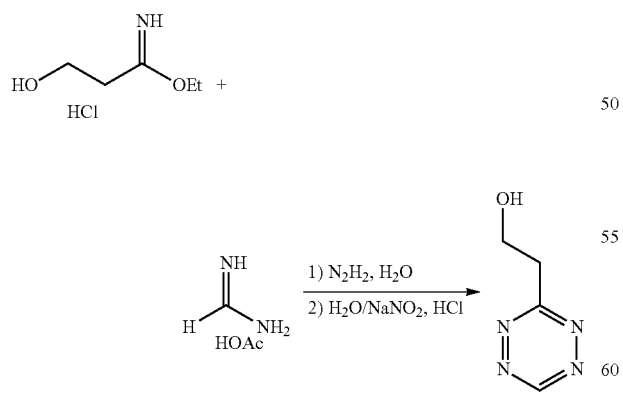

To a mixture of ethyl 3-hydroxypropanimidate hydrochloride (1 mmol, 153 mg) and formamidine acetate (5 mmol, 521 mg) was added hydrazine hydrate (1 mL) under an atmosphere of argon. After stirring at room temperature for 2 hours, the mixture was diluted with water (10 mL) and sodium nitrite (12.5 mmol, 0.86 g) was added. To this solution was added 2% aqueous HCl dropwise on an ice bath until the now pink solution reached a pH of 3. The aqueous solution was extracted with methylene chloride (5×25 mL), dried with magnesium sulfate, the solvent was removed by rotary evaporation, and then dried under vacuum to afford the product, 2-(1,2,4,5-tetrazin-3-yl)ethanol (28 mg, 22%), as a pink oil. LRMS-ESI [M+H]$^+$ calcd. for $C_4H_7N_4O^+$: 127.06, found: 126.7.

Example 7

5-(6-Methyl-1,2,4,5-tetrazin-3-yl)pentan-1-amine hydrochloride

The following example describes an exemplary method of synthesis of 5-(6-Methyl-1,2,4,5-tetrazin-3-yl)pentan-1-amine hydrochloride.

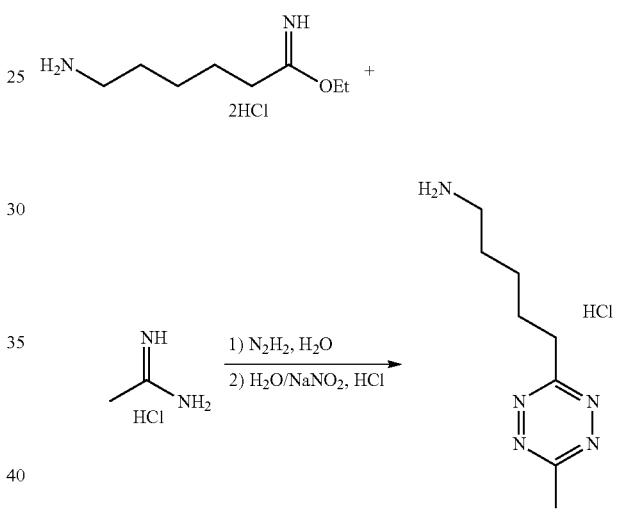

To a mixture of ethyl 6-aminohexanimidate dihydrochloride (2 mmol, 462 mg) and acetamidine hydrochloride (10 mmol, 945 mg) was added hydrazine hydrate (2 mL) under an atmosphere of argon. After stirring at room temperature for 2 hours, the mixture was diluted with water (25 mL) and sodium nitrite (25 mmol, 1.72 g) was added. To this solution was added 2% aqueous HCl dropwise on an ice bath until the pink solution reached a pH of 3. The aqueous solution was then basified to pH 12 by dropwise addition of 10% aqueous NaOH on an ice bath. The basic solution was extracted with methylene chloride (4×25 mL), dried with magnesium sulfate, and the solvent was removed by rotary evaporation. Preparative HPLC using a gradient of 0 to 25% buffer B (buffer A is water with 0.1% TFA, and buffer B is acetonitrile with 10% water and 0.1% TFA) afforded the trifluoroacetate salt of the tetrazine. This material was then loaded on a reverse phase C18 column, washed with 0.1% aqueous HCl, and eluted with a 1:1 mixture of methanol and 0.1% aqueous HCl to afford pure 5-(6-methyl-1,2,4,5-tetrazin-3-yl)pentan-1-amine hydrochloride (100 mg, 23%), as a pink solid. LRMS-ESI [M+H]$^+$ calcd. for $C_8H_{16}N_5^+$: 182.14, found: 182.0.

Example 8

5-(1,2,4,5-Tetrazin-3-yl)pentan-1-amine hydrochloride

The following example describes an exemplary method of synthesis of 5-(1,2,4,5-Tetrazin-3-yl)pentan-1-amine hydrochloride.

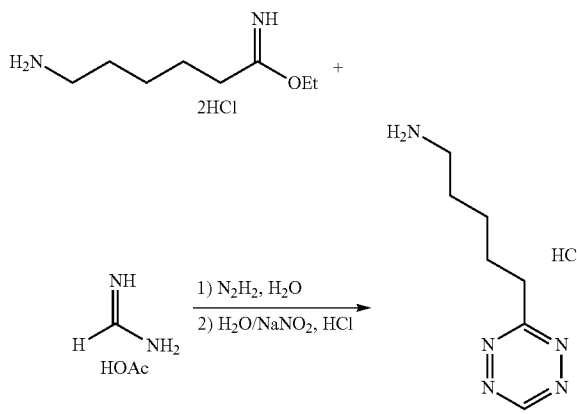

To a mixture of ethyl 6-aminohexanimidate dihydrochloride (2 mmol, 462 mg) and formamidine acetate (10 mmol, 1.04 g) was added hydrazine hydrate (2 mL) under an atmosphere of Argon. After stirring at room temperature for 2 hours, the mixture was diluted with water (25 mL) and sodium nitrite (25 mmol, 1.72 g) was added. To this solution was added 2% aqueous HCl dropwise on an ice bath until the pink solution reached a pH of 3. The solvent was removed by rotary evaporation and the residue was washed with methanol (2×25 mL). After filtration, the remaining solid was dissolved in water (25 mL) and saturated with solid $Na_2CO_3$. This solution was extracted with methylene chloride (4×25 mL). To the pink organic solution was added 250 uL TFA and the solvent was removed by rotary evaporation. Preparative HPLC using an isocratic gradient of 100% buffer A (buffer A is water with 0.1% TFA) afforded the trifluoroacetate salt of the tetrazine. This material was then loaded on a reverse phase C18 column, washed with 0.1% aqueous HCl, and eluted with a 1:1 mixture of methanol and 0.1% aqueous HCl to afford pure 5-(1,2,4,5-tetrazin-3-yl)pentan-1-amine hydrochloride (55 mg, 13.5%), as a pink solid. LRMS-ESI [M+H]$^-$ calcd. for $C_7H_{14}N_5^+$: 168.12, found: 167.8.

Example 9

2-(6-(Pyridin-2-yl)-1,2,4,5-tetrazin-3-yl)ethanol

The following example describes an exemplary method of synthesis of 2-(6-(Pyridin-2-yl)-1,2,4,5-tetrazin-3-yl)ethanol.

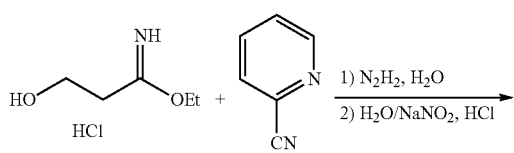

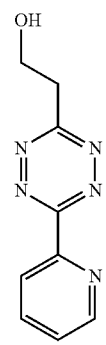

To a mixture of ethyl 3-hydroxypropanimidate hydrochloride (1 mmol, 153 mg) and 2-pyridinecarbonitrile (5 mmol, 520 mg) was added hydrazine hydrate (1 mL). After stirring at 90° C. for 1 hour, the mixture was cooled, diluted with water (10 mL), filtered, and to the filtrate was added sodium nitrite (10 mmol, 0.69 g) with stirring. To this pink solution was added 2% aqueous HCl dropwise on an ice bath until the solution reached a pH of 3. The solution was dried by rotary evaporation, the residue was washed with methanol (2×10 mL), filtered, and the filtrate was dried by rotary evaporation. Column chromatography on silica gel eluting with 1.5% methanol in methylene chloride afforded pure 2-(6-(pyridin-2-yl)-1,2,4,5-tetrazin-3-yl)ethanol (44 mg, 22%), as a pink solid. LRMS-ESI [M+H]$^+$ calcd. for $C_9H_{10}N_5O^+$: 204.09, found: 203.9.

Example 10

2-(6-(Pyrimidin-2-yl)-1,2,4,5-tetrazin-3-yl)ethanol

The following example describes an exemplary method of synthesis of 2-(6-(Pyrimidin-2-yl)-1,2,4,5-tetrazin-3-yl)ethanol.

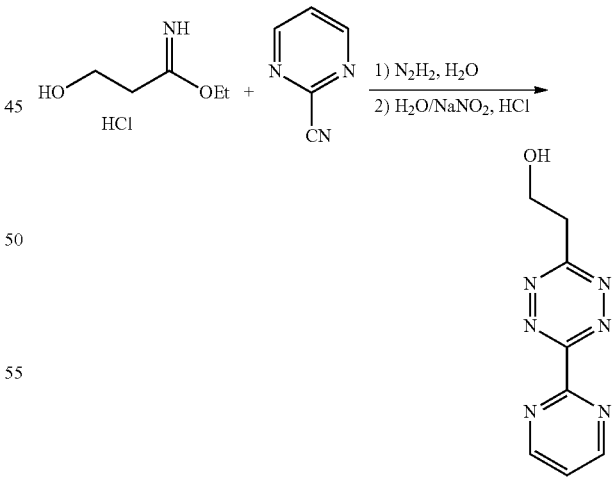

To a mixture of ethyl 3-hydroxypropanimidate hydrochloride (1 mmol, 153 mg) and 2-Pyrimidinecarbonitrile (5 mmol, 525 mg) was added hydrazine hydrate (1 mL). After stirring at 90° C. for 1 hour, the mixture was cooled, diluted with water (10 mL), filtered, and to the filtrate was added sodium nitrite (10 mmol, 0.69 g) with stirring. To this pink solution was added 2% aqueous HCl dropwise on an ice bath until the solution reached a pH of 3. The solution was dried by rotary evaporation, the residue was washed with methanol (2×10 mL), filtered, and the filtrate was dried by rotary evaporation. Column chromatography on silica gel eluting with 1.5% methanol in methylene chloride afforded pure 2-(6-(pyrimidin-2-yl)-1,2,4,5-tetrazin-3-yl)ethanol (26 mg, 12.7%), as a pink solid. LRMS-ESI [M+H]$^+$ calcd. for $C_8H_9N_6O^+$: 205.08, found: 204.9.

Example 11

4-(1,2,4,5-Tetrazin-3-yl)aniline

The following example describes an exemplary method of synthesis of 4-(1,2,4,5-Tetrazin-3-yl)aniline.

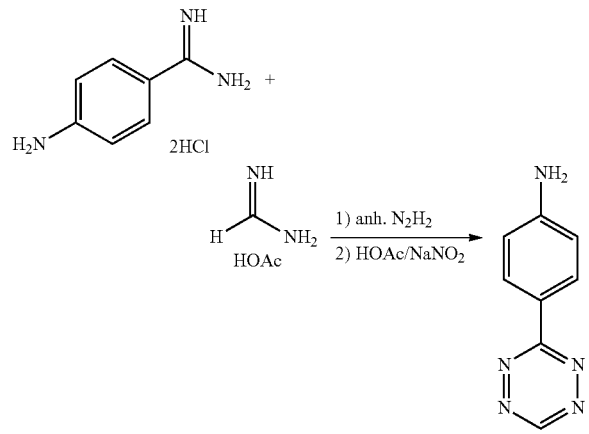

To a mixture of 4-Aminobenzamidine dihydrochloride (1 mmol, 208 mg) and formamidine acetate (4 mmol, 416 mg) in acetonitrile (25 mL) was added anhydrous hydrazine (10 mmol, 315 uL). The solution was heated to reflux for 1 hour, cooled, and the solvent was removed by rotary evaporation. The residue was resuspended with water (25 mL) and was stirred with solid tetrachloro-1,4-benzoquinone (2 mmol, 492 mg) for 1 hour. After removal of the solids from the pink solution by filtration, the reaction was concentrated by rotary evaporation and purified by preparative HPLC using a gradient from 0-40% buffer B (buffer A is water with 0.1% TFA, and buffer B is acetonitrile with 10% water and 0.1% TFA) to afford pure 4-(1,2,4,5-tetrazin-3-yl)aniline (33 mg, 19%), as a pink solid. LRMS-ESI [M+H]$^+$ calcd. for $C_8H_8N_5^+$: 174.08, found: 173.9.

Example 12

1,2,4,5-Tetrazine-3,6-diamine 1,2,4,5-Tetrazine-3,6-diamine was prepared according the procedure described in JACS 1954, 76, 427.

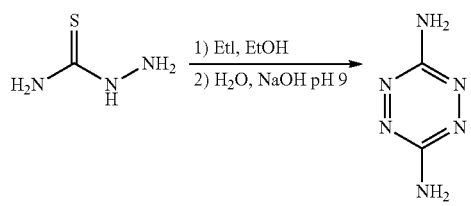 [SMILES: NNC(N)=S ; Nc1nnc(N)nn1]

Example 13

Synthesis of (E)-cyclooct-4-enyl 2,5-dioxopyrrolidin-1-yl carbonate

Part A. Synthesis of (E)-cyclooct-4-enol

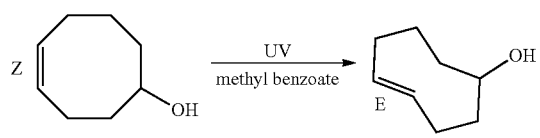 [SMILES: OC1CC/C=C\CCC1 ; "UV" ; OC1CC/C=C/CCC1]

(E)-cyclooct-4-enol was synthesized from (Z)-cyclooct-4-enol using a modification of a previously reported protocol (Royzen, M. et al. J. Am. Chem. Soc. 2008, 130, 3760-3761). Briefly, 1 gram of cyclooctenol (2) and 1.1 g methyl benzoate sensitizer was added to 250 mL solvent (9:1 Ether:Hexanes) in a 500 mL quartz reaction vessel (Southern New England Ultraviolet Company). No attempt to degas the solution was made. The vessel was irradiated with 254 nm light in a Rayonet RPR-100 UV reactor (Southern New England Ultraviolet Company) under constant stirring. At 30 minute intervals, the irradiation was stopped and the entire solution was passed through a column packed with silver nitrate (10%) impregnated silica (commercially available from Aldrich). The solution that passes through was then transferred back into the quartz flask and irradiation was continued. After 6 hours the irradiation was stopped and the silica was added to a solution of ammonium hydroxide and stirred for 5 minutes after which ether was added and stirring continued for 5 more minutes. After stirring the ether phase was decanted, washed with water, dried with magnesium sulfate, and evaporated yielding trans-cyclooctenol (40%) as a mixture of isomers as previously reported. The isomers were separated by column chromatography (1:1 Ethyl Acetate Hexanes) and verified by proton NMR using the previously reported proton NMR spectra (Royzen, M. et al. J. Am. Chem. Soc. 2008, 130, 3760-3761) The major isomer (more polar isomer) was used for the synthesis of (E)-cyclooct-4-enyl 2,5-dioxopyrrolidin-1-yl carbonate.

Part B. Synthesis of (E)-cyclooct-4-enyl 2,5-dioxopyrrolidin-1-yl carbonate

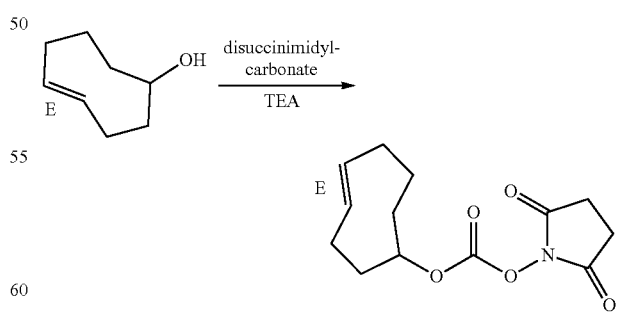

(E)-cyclooct-4-enyl 2,5-dioxopyrrolidin-1-yl carbonate. 50 mg of (E)-cyclooct-4-enol (major isomer) and 0.2 mL triethylamine were added to 3 mL anhydrous acetonitrile. To this solution was slowly added 250 mg of N,N-disuccinimidyl carbonate. The reaction mixture was stirred at room temperature until thin layer chromatography revealed that the reaction was complete (approximately 48 hours). The acetonitrile was removed by rotary evaporation and the remaining residue was suspended in ether, washed with 0.1M HCl followed by brine, and dried with magnesium sulfate. The ether was evaporated and the resulting oil was purified by column chromatography (1:1 Ethyl Acetate:Hexane) yielding 80 mg (75% yield) of the title compound. $^1$H NMR (400 MHz CDCl$_3$): δ 5.65-5.54 (m, 1H), 5.5-5.4 (m, 1H), 4.5-4.4 (m, 1H), 2.88-2.78 (s, 4H), 2.45-2.3 (m, 2H), 2.2-1.5 (m, 8H).

Example 14

Synthesis of (E)-9-oxabicyclo[6.1.0]non-4-ene

The following example describes an exemplary method of synthesis of (E)-9-oxabicyclo[6.1.0]non-4-ene.

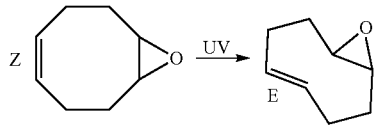

To a 9:1 ether/hexanes solution (250 mL) in a 500 mL quartz reaction vessel, was added (Z)-9-oxabicyclo[6.1.0]non-4-ene (1.0 g) and methyl benzoate (1.1 g) sensitizer. No attempt to degas the solution was made. The vessel was irradiated with 254 nm light in a Rayonet RPR-100 UV reactor (Southern New England Ultraviolet Company) under constant stirring. At 30 minute intervals, the irradiation was stopped and the entire solution was passed through a column packed with silver nitrate (10%) impregnated silica. The solution that passes through was then transferred back into the quartz flask and irradiation was continued. After 6 hours the irradiation was stopped and the silica was added to a solution of ammonium hydroxide and stirred for 5 minutes after which ether was added and stirring continued for 5 more minutes. After stirring the ether phase was decanted, washed with water, dried with magnesium sulfate, and evaporated yielding (E)-9-oxabicyclo[6.1.0]non-4-ene (0.4 g, 40% yield). $^1$HNMR (400 MHz CDCl$_3$): δ 5.8-5.7 (m, 1H), 5.4-5.2 (m, 1H), 2.9-2.7 (m, 2H) 2.5-2.0 (m, 8H).

Example 15

Fluorogenic Tetrazine-Fluorophore Cycloaddition Reactions

Tetrazines conjugated to highly charged carbocyanine-based near-IR emitting fluorophores are useful in extracellular labeling. In an effort to explore the utility of this methodology to intracellular labeling, benzylamino tetrazine was conjugated to the succinimidyl esters of visible light emitting boron-dipyrromethene (BODIPY) dyes. BODIPY dyes are uncharged and lipophilic and for these reasons have seen use in intracellular applications (Cole et al., 2000, J Microsc, 197, 239-49; Farinas and Verkman, 1999, J Biol Chem, 274, 7603-6; Miller et al., 2006, Nat Protoc, 1, 824-7; Takahashi et al., 2002, Diabetes, 51 Suppl 1, S25-8; Viht et al., 2003, Bioorg Med Chem Lett, 13, 3035-9). Unexpectedly, the tetrazine BODIPY conjugates strongly reduced fluorescence compared to the parent succinimidyl esters. Upon reaction with a strained dienophile such as trans-cyclooctenol or norbornene, the fluorescence was "switched" back on (a process referred to herein as "fluorogenic activation").

Figure 3:
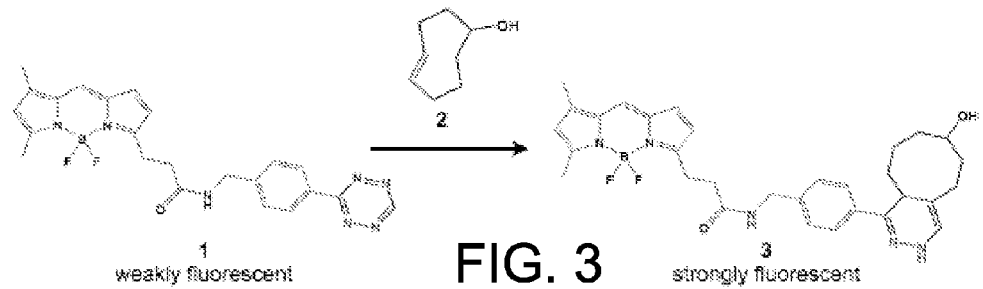
FIG. 3 shows the inverse electron demand Diels-Alder cycloadducts, dye-tetrazine conjugate and trans-cyclooctenol and the cycloaddition product.
Figure 4:
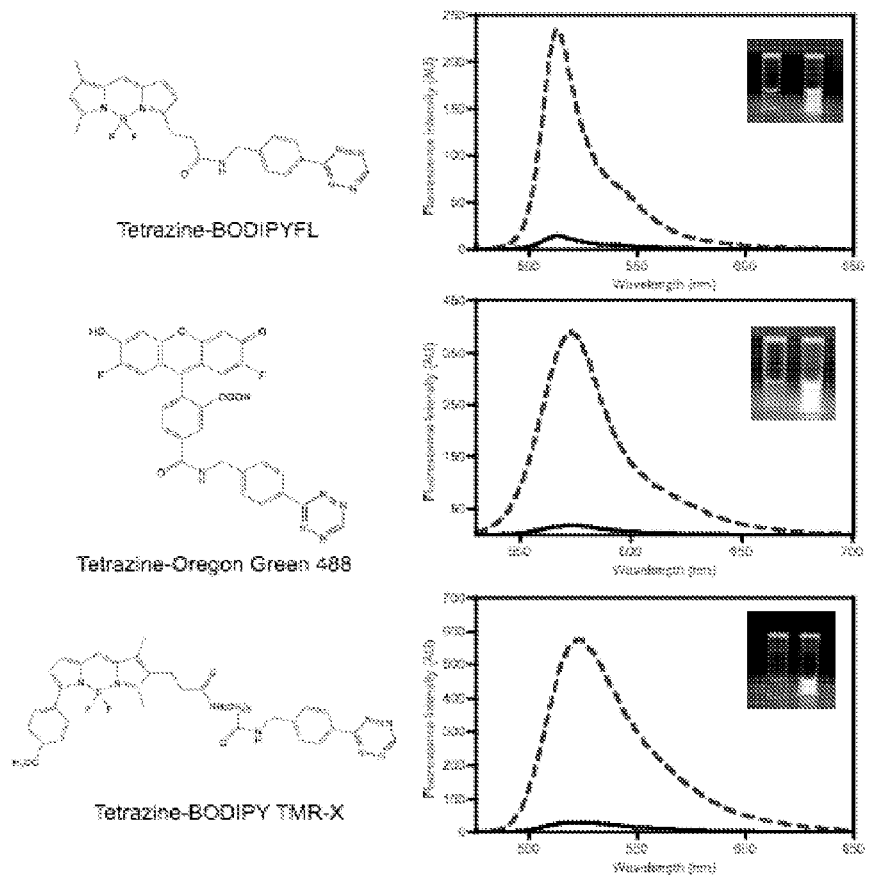
FIG. 4 shows the absorption and emission spectra of the dye-tetrazine conjugates before and after cycloaddition to trans-cyclooctenol.

To explore the generality of this methodology with other dyes, benzylamino tetrazine was reacted with the commercially available succinimidyl esters of 7-N, N-diethylaminocoumarin, BODIPY FL, BODIPY TMR-X, Oregon Green 488 and BODIPY 650-665 (Invitrogen, see FIG. 4 for structures of the tetrazine products). FIG. 4 shows emission spectra of the dye-tetrazine conjugates before and after cycloaddition to trans-cyclooctenol. As shown in FIG. 3, tetrazine-BODIPY FL (1) reacted rapidly with trans-cyclooctenol (2) via an inverse electron demand Diels-Alder cycloaddition to form isomeric dihydropyrazine products (3). The emission spectra of various tetrazine probes (black lines) and the corresponding dihydropyrazine products (dashed blue lines) were collected (FIG. 4). Inset images compare the visible fluorescence emission of the tetrazine probes (left cuvettes) to their corresponding dihydropyrazine products (right cuvettes) under excitation from a handheld UV lamp. FIG. 5 lists the photophysical properties of the dyes before and after reaction. All measurements were taken in PBS and pH 7.4 (tetrazine-fluorophore concentration 1 μM). Of note, there are no significant changes in the fluorophore absorption spectra after addition of trans-cyclooctenol (10 μM). Quantum yield measurements were obtained in triplicate with fluorescein (in water, pH 10), and Rhodamine 6G (in EtOH) as standards. Quenching of the fluorophore by the tetrazine is wavelength dependent. Green and red emitting tetrazine dyes showed fluorescent enhancements upon cycloaddition.

For all dyes emitting in the visible spectrum (400-600 nm) conjugation to the tetrazine caused fluorescence quenching, which was restored after reaction with dienophiles. This quenching may be the result of photoinduced electron transfer (PET) from the excited fluorophore to the electron poor tetrazine acceptor. Tetrazines are well know to be an electron-poor class of heterocycles, hence their utility in inverse-electron demand cycloadditions. This PET quenching would be reminiscent of the well known quenching of fluorophores by electron poor nitrated compounds (Goodpaster and McGuffin, 2001, Anal Chem, 73, 2004-11; Kim et al., 2004, J Am Chem Soc, 126, 452-3). Of particular note, these fluorogenic compounds can be formed from commercially available cores and the tetrazine appears to be a strong enough quencher that it does require intimate connection to the fluorophore and can achieve a quenching effect even when separated by aliphatic spacers.

Example 16

Tracking and Imaging a Small Molecule (Taxol®)

Synthesis of the Trans-Cyclooctene Taxol Analog

Although the use of fluorogenic probes could have a myriad of applications, one use that would immediately benefit from a fluorogenic probe is the detection of small molecules inside live cells. To test if our fluorogenic tetrazines would be relevant for imaging intracellular molecular targets, we chose dienophile-modified paclitaxel (Taxol®) as a test system. Taxol® was selected because of its tremendous clinical impact, the large body of prior work that serves as reference, and because of its well studied ability to stabilize microtubules, providing a well-defined intracellular structure to image (Evangelio et al., 1998, Cell Motil Cytoskeleton, 39, 73-90; Guy et al., 1996, Chem Biol, 3, 1021-31; Manfredi et al., 1982, J Cell Biol, 94, 688-96; Nicolaou et al., 1994, Angew. Chem. Int. Ed., 33, 15-44; Rowinsky et al., 1990, J. Natl. Cancer Inst., 82, 1247-1259; Souto et al., 1995, Angew. Chem. Int. Ed., 34, 2710-2712). The trans-cyclooctene taxol derivative (FIG. 6a) was synthesized by coupling trans-cyclooctene succinimidyl carbonate to 7-β-alanyl taxol via reported procedures (Guy et al., 1996, Chem Biol, 3, 1021-31). The dienophile was introduced in the C7 position since prior structure activity relationship studies have established that modifications at the C7 position do not significantly affect the biological activity of taxol (Chen et al., 1994, Bioorg. Med. Chem. Lett., 4, 2223-2228; Guy et al., 1996, Chem Biol, 3, 1021-31; Mellado et al., 1984, Biochem Biophys Res Commun, 124, 329-36; Souto et al., 1995, Angew. Chem. Int. Ed., 34, 2710-2712).

Briefly, 7-β-alanyltaxol was dissolved in anhydrous acetonitrile and reacted overnight at room temperature with (E)-cyclooct-4-enyl 2,5-dioxopyrrolidin-1-yl carbonate. After reaction, the acetonitrile was removed by rotary evaporation and the product isolated by column chromatography (17 mg). $^1$HNMR (400 MHz CDCl$_3$): δ 8.14-8.06 (d, 2H), 7.8-7.7 (d, 2H), 7.66-7.56 (t, 1H), 7.54-7.3 (m, 10H) 7.1-7.0 (d, 1H), 6.3-6.1 (m, 2H), 5.85-5.75 (d, 1H), 5.7-5.6 (d, 1H), 5.6-5.4 (m, 3H), 5-4.85 (d, 1H), 4.85-4.75 (m, 1H), 4.4-4.25 (m, 2H), 4.25-4.1 (d 1H), 3.95-3.85 (d, 1H), 3.65-3.55 (d, 1H), 1-3 (m 38H). LRMS-ESI [M+H]+ calcd. mass 1077.5. found 1077.7; [M+Na]+ calcd. mass 1099.4. found 1099.6.

The trans-cyclooctene taxol rapidly reacts with our tetrazine probes forming isomeric dihydropyrazine products, which can be detected by conventional means, such as LC-MS.

Testing Trans-Cyclooctene Taxol Analog in Tubulin Polymerization Assay

To test the activity of the trans-cyclooctene taxol analog, we tested for the well known ability of Taxol® to polymerize tubulin in the absence of GTP (Shelanski et al., 1973, Proc Natl Acad Sci USA, 70, 765-8; Schiff and Horwitz, 1981, Biochemistry, 20, 3247-52). Optical density measurements at 350 nm (FIG. 6B) were used to determine the degree of tubulin polymerization after exposure of tubulin monomer to Taxol®, trans-cyclooctene taxol, and a DMSO control. Both native Taxol® and trans-cyclooctene taxol induced polymerization compared to a DMSO control. Taxol trans-cyclooctene induced tubule bundles could be visualized by subsequent staining with tetrazine fluorophore probes such as tetrazine-BODIPY FL yielding brightly fluorescent tubule structures that could be imaged by fluorescent microscopy (FIG. 6c).

Testing Trans-Cyclooctene Taxol Analog in PtK2 Rat Kidney Cells

For live cell studies, PtK2 rat kidney cells were incubated in cell media containing 1 μM trans-cyclooctene taxol for 1 hour at 37° C. After washing with media three times, the cells were exposed to media containing 1 μM tetrazine-BODIPY FL for 20 minutes at room temperature. The cells were then washed and imaged on a confocal microscope. Confocal microscopy of the PTK2 rat kangaroo cell after treatment with 1 μM trans-cyclooctene-taxol followed by 1 μM tetrazine-BODIPY FL showed that tubular structures were clearly stained. Confocal microscopy of PTK2 cells after treatment with only 1 μM trans-cyclooctene-taxol followed by 1 μM tetrazine-VT680 showed intracellular structures reflecting microtubule networks. Taxol® is known to bind the microtubular networks of cells and there have been several reports of fluorescent taxol derivatives that can be used to image microtubular networks (Evangelio et al., 1998, Cell Motil Cytoskeleton, 39, 73-90; Guy et al., 1996, Chem Biol, 3, 1021-31; Souto et al., 1995, Angew. Chem. Int. Ed., 34, 2710-2712). In addition to tubular structures, the perinuclear region was stained. This staining is due to nonspecific uptake of the taxol analog by intracellular membranes such as the endoplasmic reticulum and Golgi. Control experiments employing tetrazine-BODIPY FL alone or with unmodified taxol yielded minimal fluorescent background and demonstrated that there is little non-specific or background turn-on and that the images resulted from specific tetrazine trans-cyclooctene reaction. Furthermore, cells treated with trans-cyclooctene followed by highly charged non-membrane permeable tetrazine probes such as sulfonated Vivo-Tag 680 tetrazine showed very little staining and an absence of tubular structures, giving further evidence that tetrazine-BODIPY FL is able to penetrate the cell membrane and label trans-cyclooctene located within the cell (Devaraj et al., 2009, Angew Chem Int Ed Engl, 48, 7013-6; Devaraj et al., 2008, Bioconjug Chem, 19, 2297-9).

Example 17

Synthesis of other Bioconjugatable trans-cyclooctene Derivatives that are Analogous to the norbornene (1S,2S,4S)-bicyclo[2.2.1]hept-5-en-2-yl acetic Acid)

Epoxides like the one in the trans-cyclooctene product are reactive with nucleophiles such as amines and thiols and are used as is for attachment of the trans-octene to other biomolecules.

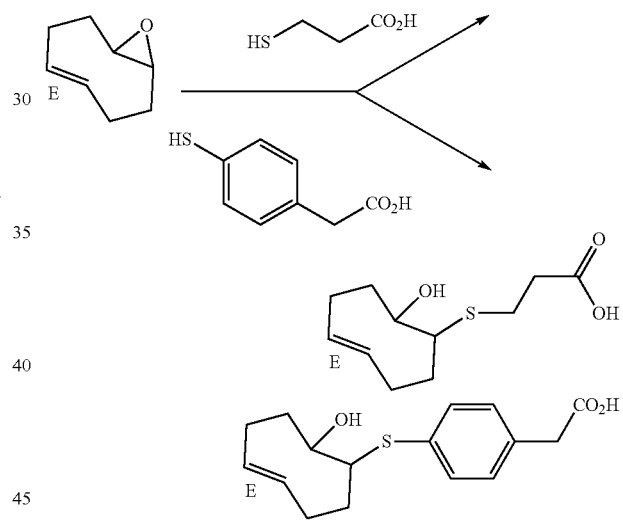

Via standard procedures, alkyl-thiols (3-mercaptopropanoic acid, 2-(4-mercaptophenyl)acetic acid, etc.) or other nucleophiles containing additional functional groups such as, but not limited to carboxylic acids may be coupled to (E)-9-oxabicyclo[6.1.0]non-4-ene via nucleophilic attack and subsequent ring opening of the epoxide functionality of (E)-9-oxabicyclo[6.1.0]non-4-ene to yield corresponding carboxylic acid functionalized trans-cyclooctenes where the carboxylic acid functionality is linked to the cyclooctene via a chemically stable thioether bond. These synthetic procedures use standard procedures to generate new compounds in which the carboxylic acid (or other functional groups) is connected to the trans-octene by a chemically stable linker. This route also generates a secondary alcohol (OH group) on the trans-octene that may help improve the aqueous solubility by making the compound more polar.

For example, (E)-2-(4-(8-hydroxycyclooct-4-enylthio) phenyl)acetic acid (as shown in the lower reaction path in the scheme above) is prepared by the reaction of 2-(4-mercaptophenyl)acetic acid (21.0 mg, 0.125 mmol) with (E)-9-oxabicyclo[6.1.0]non-4-ene (15.5 mg, 0.125 mmol) in a mixture of acetonitrile (100 µL) and water (200 µL) with 20 mol % ZnCl$_2$ as catalyst. After stirring the biphasic mixture for 1 hour, the product is isolated by removal of the solvents under vacuum. LRMS-ESI [M+H]$^+$ calcd. for C$_{16}$H$_{21}$O$_3$S$^+$: 293.12, found: 293.1.

Example 18

Preparation of Aminoalcohols

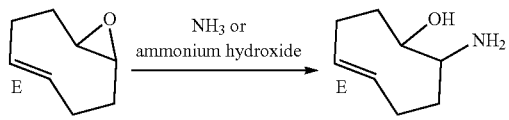 [SMILES: C1=C/CCC2OC2CC/1 ; NC1CC/C=C/CCC1O]

This nucleophilic attack is adaptable to preparing amine-modified trans-cyclooctenes via nucleophilic attack of ammonia (or primary and secondary amines) on the epoxide of (E)-9-oxabicyclo[6.1.0]non-4-ene.

Example 19

Protein Labeling

Proteins such as, but not limited to, horseradish peroxidase (HRP) are labeled with the succinimidyl esters of the dienophile or tetrazine coupling components. HRP in aqueous buffer is treated with the succinimidyl ester of 5-(4-(1,2,4,5-tetrazin-3-yl)benzylamino)-5-oxopentanoic acid (prepared by treatment of 5-(4-(1,2,4,5-tetrazin-3-yl)benzylamino)-5-oxopentanoic acid with disuccinimidyl carbonate in the presence of pyridine) to form tetrazine modified HRP (HRP-tetrazine).

Example 20

Antibody Labeling

Antibodies such as, but not limited to, trastuzumab, were labeled with the succinimidyl esters of the dienophile or tetrazine coupling components. Trastuzumab in aqueous buffer was treated with a 30 molar excess of the succinimidyl ester of ((1S,2S,4S)-bicyclo[2.2.1]hept-5-en-2-yl acetic acid) (prepared by treatment of ((1S,2S,4S)-bicyclo[2.2.1] hept-5-en-2-yl acetic acid) in acetonitrile with 1.1 equiv of disuccinimidyl carbonate and 1 equiv of pyridine) to form ((1S,2S,4S)-bicyclo[2.2.1]hept-5-en-2-yl acetic acid) modified trastuzumab (mAb-norbornene).

Example 21

Pretargeting Methods Using an Anti-EGFR Antibody

An anti-EGFR antibody (cetuximab) was labeled with trans-cyclooctene succinimidyl carbonate and used for pretargeting experiments as follows.
Labeling Antibody with Trans-Cyclooctene
Cetuximab (ImClone 2 mg/mL) was purchased and the solvent exchanged for 0.1M NaHCO$_3$ buffered at pH 8.5 with a final concentration of 7 mg/mL. To 200 uL of this stock solution was added 10 uL of DMF. (E)-cyclooct-4-enyl 2,5-dioxopyrrolidin-1-yl carbonate was dissolved in anhydrous DMF to make a 40 mM stock solution. For conjugation, the appropriate excess of amine reactive trans-cyclooctene in DMF was aliquoted into the antibody solution, vortexed, and reacted overnight at 4° C. In the experiments reported, the final trans-cycloctene loadings of 1, 3, 5, and 6 correspond to using 2, 10, 30, and 100 equivalents of succinimidyl carbonate with respect to antibody. After overnight reaction the antibodies were purified by centrifuge filtration using 5% DMSO PBS, concentrated to 2 mg/mL and stored in PBS at 4° C.

Antibody Labeling with Fluorescent Succinimidyl Esters
A solution of antibody (1 mg/mL) in 0.1M NaHCO$_3$ (pH 8.5) was incubated with 2 equivalents of fluorescent succinimidyl ester (VT680, AF555, or Dylight 488) for 2 hours. After incubation, the antibody was purified by centrifuge filtration using 30000 dalton molecular weight cutoff filters (Amicon) and stored in PBS. The number of fluorochromes per antibody was determined by spectrophotometric analysis and determined to be approximately 1 per antibody for all dye succinimidyl esters used.
Kinetic Measurements
trans-cyclooctene modified antibody was physically absorbed onto polystyrene by immersing the surfaces in a 0.1 mg/mL solution of antibody in PBS for 3 hours. After numerous washes with PBS, the surface was exposed to 750 nM tetrazine VT680 in PBS at 37° C. After 5 minutes, the tetrazine solution was removed and the surface washed 3 times with PBS. The fluorescence due to the VT680 dye was measured on a fluorescence plate reader (Tecan Safire 2) and corrected for background fluorescence. The surface was again exposed to the tetrazine solution and the entire process repeated at 10, 15, 30, and 60 minutes. The fluorescence measurements were plotted versus time, fitted to a first order exponential growth curve and the pseudo first order rate constant determined The entire experiment was repeated using two different concentrations of tetrazine (375 nM and 1000 nM) and the pseudo first order rate constants from all three experiments were plotted versus concentration, fitted to a straight line; the slope of the line was 6000±200 M−1sec−1 and was reported at the second order rate constant for the reaction between tetrazine VT680 and trans-cyclooctene bound to antibody.
Cell Culture
The human lung adenocarcinoma epithelial cell line A549 was selected for all experiments due to its mid-level overexpression of EGFR. The cell line was maintained in a standard ATCC formulated F-12K media supplemented with 10% fetal bovine serum and 5% penicillin/streptomycin. In order to facilitate microscopy and visualize intracellular morphology, EGFP labeling of the cell line was done using a third-generation lentiviral vector system. 293T cells were transfected using lipofectamine 2000 in a subconfluent 10-cm dish with the vector pCCLsin.PPT.hPGK (10 ug), into which EGFP had been cloned, as well as pMDLg/p packaging (7 ug) and VSV-G envelope encoding pMD.G (5 ug) plasmids. These plasmids were obtained from Rafaella Sordella at the MGH Center for Cancer Research and Luigi Naldini at the San Raffaele Telethon Institute for Gene Therapy. Viral supernatant was collected after 48 hours, filtered with a 0.45 micron syringe filter, and stored at −80° C. The A549 cell line was infected in subconfluent wells of 24-well plates, using 300 uL of virus in 1 mL of F-12K culture media with 10% fetal calf serum. This protocol yielded an infection rate in excess of 80% (determined by visual assessment using fluorescence microscopy). EGFP-negative cells were removed using a modified 5-laser Becton-Dickinson FACSDiVa with standard techniques.

Confocal Microscopy

Cells were grown on break away glass chamber slides and washed six times after administering either imaging agent. A multichannel upright laser-scanning confocal microscope (FV1000; Olympus) was used to image live cells with a 60× water immersion objective lens. Image collection and fluorophore excitations with lasers at 488 nm (EGFP), 543 nm (AF555), and 633 nm (VT680) were done serially to avoid cross talk between channels. Data were acquired with Fluoview software (version 4.3; Olympus) and image stacks were processed and analyzed with ImageJ software (version 1.41, Bethesda Md.).

Direct labeling of the antibodies with AF555 was monitored in the red channel. The antibody was clearly visible both on the surface of the cells and inside the cells as a result of EGFR internalization (Vincenzi et al., Rev. Oncol. Hematol. 68:93-106 (2008); Patel et al., Anticancer Res. 27:3355-3366 (2007). Covalently bound tetrazine-VT680 could be visualized clearly in the near-infrared (NIR) channel. Merging of the red and NIR channels revealed excellent colocalization of the AF555 and VT680 signals with little background fluorescence. This result indicates that the reaction of the tetrazine is extremely selective. As expected, the reaction occurred primarily on the surface of the cells, where EGFR concentrations are highest. A smaller amount of cell-internalized, vesicle-associated NIR fluorescence was also observed. This fluorescence is probably a result of EGFR internalization after treatment with tetrazine-VT680 (Vincenzi et al., supra, 2008, and Patelt et al., supra, 2007). Control experiments with either unlabeled cetuximab and tetrazine-VT680 or trans-cyclooctene-cetuximab and unlabeled VT680 resulted in no NIR fluorescence.

Next, labeling was observed without a washing step to remove the probe. The desire to avoid such a step is relevant to applications in which one is unable to perform stringent and multiple washing steps, such as intracellular labeling, experiments in which cell handling has to be minimized (with rare cells or highly specialized cells), and in vivo labeling. The concentration of the tetrazine-VT680 label was lowered to 50 nm to enable observation of the covalent modification in real time. The images were taken during continuous imaging of the cycloaddition of the tetrazine-VT680 to the pretargeted trans-cyclooctene on live cancer cells in 100% FBS. Tetrazine-VT680 first became visible as it reacted and concentrated on the surface of cells; at later times, punctate spots within the cell were visible as tetrazine-labeled cetuximab was internalized.

In an attempt to improve the signal-to-background ratio, the loading density of the reactive transcyclooctene on the targeted antibodies was increased. A greater number of reactive sites per antibody should lead to more fluorophore per antibody after labeling and thus result in signal amplification. To vary the trans-cyclooctene loading, we exposed cetuximab to different molar excesses of the amine-reactive trans-cyclooctene. The conjugates were modified with tetrazine-VT680, and the resulting fluorochrome absorbance was used to estimate the number of reactive trans-cyclooctene units per antibody. In this fashion, cetuximab bearing one, three, five, and six tetrazine-VT680-reactive trans-cyclooctene moieties were prepared. Owing to the large size of indocyanine dyes, for the higher loadings, the number of reactive trans-cyclooctene moieties is probably lower than the actual number of trans-cyclooctene moieties on the antibody. These trans-cyclooctene-cetuximab conjugates bound to EGFR-expressing A549 cells with excellent stability.

Flow Cytometry

To illustrate the practical effect of this amplification on the imaging of live cells, flow cytometry was used to gain a more quantitative understanding of live-cell fluorescent labeling with the tetrazine. Confluent A549 cells were suspended using 0.05% Tryspin/0.53 mM EDTA, washed by centrifugation with PBS containing 2% FBS (PBS+), and 2.5×10$^5$ cells were added to microcentrifuge tubes. Cetuximab antibody with the following modifications was then added at 10 ug/ml concentration in 100 uL PBS+: none (control), 1 trans-cyclooctene per antibody, 3 trans-cyclooctene per antibody, 5 trans-cyclooctene per antibody, 6 trans-cyclooctene per antibody. The cycloaddition was carried out with tetrazine-VT680 (500 nm) at 37 8 C in 100% FBS. Following incubation for 15 or 30 minutes at room temperature, samples were washed with PBS+. For stability studies, trans-cyclooctene antibodies were labeled with Dylight 488 fluorophore (Pierce, ~1 per antibody) and the cells were resuspended in 100 uL PBS+ and incubated for 15, 30, or 60 minutes at 37° C. before addition of 1 ml PBS+ and 2 washes by centrifugation. For clicking studies, labeled cells were resuspended in 100 uL FBS containing 500 nM tetrazine-VT680 and incubated for 30 minutes at 37° C. before addition of 1 ml PBS+ and 2 washes by centrifugation. VT680 and DyeLight-488 fluorescence was assessed using an LSRII flow cytometer (Becton Dickinson) and analyzed using FlowJo software.

Cells pretargeted with trans-cyclooctene-conjugated cetuximab constructs with higher loadings of the trans-cyclooctene were visualized readily, and the signal diminished as the amount of the dienophile on the antibody decreased. The ability to amplify signals by loading increased amounts of a small molecule on the antibody provides a strategy for increasing the signal-to-background ratio for in vivo pretargeting schemes.

Thus, this provides a highly sensitive technique for the covalent labeling of live cancer cells on the basis of the cycloaddition of a tetrazine to a highly strained trans-cyclooctene.

Example 22

Pretargeting Methods using an Anti-HER2/neu Antibody

To demonstrate the use of the tetrazine-dienophile reaction for live-cell labeling, the FDA-approved monoclonal antibody trastuzumab (Herceptin), which binds to Her2/neu growth factor receptors (Lewis et al., Cancer Immunol. Immun 37, 255-263 (1993)), was used. Trastuzimab was simultaneously labeled with norbornene and tetramethyl rhodamine using standard coupling conditions.

General Materials and Methods

All chemicals were purchased from Sigma Aldrich unless noted and were used as received. The norbornene, (1S,2S, 4S)-bicyclo[2.2.1]hept-5-en-2-yl acetic acid, was purchased from ChemBridge. All solvents were of reagent grade or higher and were used without further purification. Analytical HPLC and LC/MS were performed on a Waters 2695 HPLC equipped with a 2996 diode array detector, a Micromass ZQ4000 ESI-MS module, and a Grace-Vydac RPC18 column (model 218TP5210) at a flow rate of 0.3 mL/minute. Preparative HPLC was performed on a Varian ProStar model 210 instrument equipped with a model 335 diode array detector, a model 701 fraction collector, and a Varian RPC18 column (model A6002250X212) at a flow rate of 21 mL/minute. For all HPLC runs, solvent A consists of water with 0.1% TFA and solvent B is composed of acetonitrile with 10% water and 0.1% TFA. All UV/vis spectra and kinetics experiments were recorded on an Agilent 8453 diode array UV/vis spectrophotometer. Pseudo first order rate constants from all kinetics experiments were calculated using the Agilent UV/vis Chemstation software package Rev. A.10.01. Fluorescence measurements were obtained using a Varian Cary Eclipse fluorescence spectrophotometer. 1H (400 MHz) and 13C NMR (100 MHz) spectra were collected on a Bruker Advance-400 NMR spectrometer at ambient temperature in D2O with 3-(trimethylsilyl)-propionic-2,2,3,3-D4 acid sodium salt (TSP) as an internal standard. High-resolution electrospray ionization (ESI) mass spectra were obtained on a Bruker Daltonics APEXIV 4.7 Tesla Fourier transform mass spectrometer (FT-ICR-MS).

Antibody Labeling

Norbornene carboxylic acid ((1S,2S,4S)-bicyclo[2.2.1]hept-5-en-2-yl acetic acid) was stirred for three hours with 1.1 equivalents of disuccinimidyl carbonate in acetontrile using 1 equivalent of pyridine as base. After reaction, solvent and base were removed by rotary evaporation and the crude norbornene succinimidyl ester with N-hydroxysuccinimide side product was recovered. Commercially purchased humanized anti-HER2/neu antibody trastuzumab (Genentech, San Francisco, Calif.) in 0.1M sodium bicarbonate buffer (pH 8.2) was incubated for three hours at room temperature with a 5 molar excess of 5-(and-6)-carboxytetramethylrhodamine, succinimidyl ester (Invitrogen) and a 30 molar excess of crude norbornene succinimidyl ester. The antibody was then isolated and washed by centrifuge purification and stored in PBS buffer. Control antibody was modified in an identical manner but excluding the norbornene NHS.

Cell Labeling and Imaging

SKBR-3 human mammary carcinoma cell lines were maintained in complete McCoy's medium. Cells were incubated at 37° C. with 200 nM modified trastuzumab for 30 minutes and then washed twice with 10% fetal bovine serum (FBS) in Hanks balanced salt solution (HBSS). Tetrazine labeling was performed by incubating the cells for 30 minutes at 37° C. in 10% FBS/HBSS containing 50 µM of tetrazine-VT680. Cells were then washed twice with 10% FBS/HBSS and imaged with by fluorescence microscopy.

After washing, the cells were imaged using both rhodamine and NIR fluorescence channels. Significant labeling, which colocalizes, was observed. Cells incubated with a control antibody, which contained rhodamine but not norbornene, showed no NIR labeling after exposure to 3. These experiments demonstrate the specificity of the tetrazine imaging agent for norbornene-modified antibody in the presence of live cells and serum. The reaction is rapid even with micromolar concentrations of the labeling agent and importantly in the presence of serum. These findings clearly indicate that this chemistry is suitable for in vitro experiments and is a useful strategy for in vivo imaging under numerous modalities.

Example 23

Nanoparticle Labeling

Nanoparticles containing amino functionality are labeled with the succinimidyl esters of the dienophile or tetrazine coupling components Amine modified cross-linked iron oxide (CLIO—NH$_2$) nanoparticles are functionalized with the succinimidyl esters of the dienophile component by treatment of the CLIO—NH$_2$ with the succinimidyl ester of ((1S, 2S,4S)-bicyclo[2.2.1]hept-5-en-2-yl acetic acid) in aqueous buffer followed by purification by centrifugal filtration or size exclusion chromatography.

Example 24

Immunohistochemistry (IHC) Staining

The compositions described herein are useful in immunohistochemistry methods.

Example A

Treat the tissue section with 0.3% H$_2$O$_2$ in water for 30 minutes to quench endogenous peroxidase activity. Wash the section for 5 minutes with PBS, remove the buffer, and repeat the washing two additional times. The tissue section is then incubated with unlabeled primary antibody in PBS buffer for 30 minutes. Unbound and non-specifically bound antibody is removed by washing with PBS 3 times for 5 minutes each. After washing, the tissue section is incubated with 4% blocking serum in PBS for 30 minutes using serum from the species in which the secondary antibody is made. The diluted serum solution is decanted and the tissue section is washed 3 times for 5 minutes each with PBS. Then the tissue section is incubated with the dienophile modified secondary antibody (mAb-norbornene) (prepared via a procedure analogous to the example above where trastuzumab is the antibody) After washing 3 times for 5 minutes each with PBS, the tissue section is incubated with HRP-tetrazine (as prepared in the example above) in PBS buffer for 30 minutes to conjugate the secondary antibody to the HRP-tetrazine via the inverse electron demand Diels-Alder coupling reaction. The tissue section is then washed 3 times for 5 minutes each to remove unconjugated HRP-tetrazine. The tissue section is incubated with dilute H$_2$O$_2$ (typically 0.5 to 10 µM) and the appropriate chromogenic peroxidase substrate such as, but not limited to, diaminobenzidine (DAB) or 3-amino-9-ethyl carbazole (AEC) until the desired staining intensity is obtained. The procedure is completed by washing with water and mounting of the tissue section.

Example B

Treat the tissue section with 0.3% H$_2$O$_2$ in water for 30 minutes to quench endogenous peroxidase activity. Wash the section for 5 minutes with PBS, remove the buffer, and repeat the washing two additional times. The tissue section is then incubated with norbornene or trans-cyclooctene labeled primary antibody (as prepared in the example above) in PBS buffer for 30 minutes. Unbound and non-specifically bound antibody is removed by washing with PBS 3 times for 5 minutes each. After washing, the tissue section is incubated with HRP-tetrazine (as prepared in the example above) in PBS buffer for 30 minutes to conjugate the primary antibody to the HRP-tetrazine via the inverse electron demand Diels-Alder coupling reaction. The tissue section is then washed 3 times for 5 minutes each to remove unconjugated HRP-tetrazine. The tissue section is incubated with dilute H$_2$O$_2$ (typically 0.5 to 10 µM) and the appropriate chromogenic peroxidase substrate such as, but not limited to, diaminobenzidine (DAB) or 3-amino-9-ethyl carbazole (AEC) until the desired staining intensity is obtained. The procedure is completed by washing with water and mounting of the tissue section.

Example 25

Immunofluorescence Staining

The compositions described herein are useful in immunofluorescence methods.

Example A

The tissue section is first incubated with norbornene or trans-cyclooctene labeled primary antibody (as prepared in the example above) in PBS buffer for 30 minutes. Unbound and non-specifically bound antibody is removed by washing with PBS 3 times for 5 minutes each. After washing, the tissue section is incubated with a tetrazine-fluorophore conjugate (such as, but not limited to tetrazine-VT680 (as prepared in a previous example)) in PBS buffer for 30 minutes to covalently couple the fluorophore to the primary antibody. The tissue section is then washed 3 times for 5 minutes each to remove unconjugated tetrazine-VT680. The procedure is completed by washing with water and mounting of the tissue section.

Example B

The tissue section is first incubated with unlabeled primary antibody in PBS buffer for 30 minutes. Unbound and non-specifically bound antibody is removed by washing with PBS 3 times for 5 minutes each. After washing, the tissue section is incubated with 4% blocking serum in PBS for 30 minutes using serum from the species in which the secondary antibody is made. The diluted serum solution is decanted and the tissue section is washed 3 times for 5 minutes each with PBS. Then the tissue section is incubated with the dienophile modified secondary antibody (mAb-norbornene) (prepared via a procedure analogous to the example above where trastuzumab is the antibody) for 30 minutes. After washing 3 times for 5 minutes each with PBS, the tissue section is incubated with a tetrazine-fluorophore conjugate (such as, but not limited to tetrazine-VT680 (as prepared in a previous example)) in PBS buffer for 30 minutes to covalently couple the fluorophore to the primary antibody. The tissue section is then washed 3 times for 5 minutes each to remove unconjugated tetrazine-VT680. The procedure is completed by washing with water and mounting of the tissue section.

Example C

Norbornene or trans-cyclooctene labeled primary antibody (as prepared in the example above) is incubated with a tetrazine-fluorophore conjugate (such as, but not limited to tetrazine-VT680 (as prepared in a previous example)) in PBS buffer for 30 minutes to covalently couple the fluorophore to the primary antibody. If necessary this solution may be purified by centrifugal filtration. Otherwise, the crude fluorescently labeled primary antibody solution is incubated with the tissue section for 30 minutes in PBS. After incubation, unbound, non-specifically bound antibody, and any remaining tetrazine-fluorophore are removed by washing with PBS 3 times for 5 minutes each.

Example 26

Tyramide Signal Amplification (TSA) Immunofluorescence

The compositions described herein are useful in TSA immunofluorescence methods.

Example A

Treat the tissue section with 0.3% $H_2O_2$ in water for 30 minutes to quench endogenous peroxidase activity. Wash the section for 5 minutes with PBS, remove the buffer, and repeat the washing two additional times. The tissue section is then incubated with unlabeled primary antibody in PBS buffer for 30 minutes. Unbound and non-specifically bound antibody is removed by washing with PBS 3 times for 5 minutes each. After washing, the tissue section is incubated with 4% blocking serum in PBS for 30 minutes using serum from the species in which the secondary antibody is made. The diluted serum solution is decanted and the tissue section is washed 3 times for 5 minutes each with PBS. Then the tissue section is incubated with the dienophile modified secondary antibody (mAb-norbornene) (prepared via a procedure analogous to the example above where trastuzumab is the antibody) After washing 3 times for 5 minutes each with PBS, the tissue section is incubated with HRP-tetrazine (as prepared in the example above) in PBS buffer for 30 minutes to conjugate the secondary antibody to the HRP-tetrazine via the inverse electron demand Diels-Alder coupling reaction. The tissue section is then washed 3 times for 5 minutes each to remove unconjugated HRP-tetrazine. The tissue section is incubated with dilute $H_2O_2$ (typically 0.5 to 10 µM) and the appropriate tyramide conjugated fluorophore substrate such as, but not limited to, fluorescein tyramide, tetramethylrhodamine tyramide, or Cy5 tyramide. After incubation for the desired time, the procedure is completed by washing with water or PBS 3 times for 5 minutes each to remove any excess fluorophore-tyramide and mounting of the tissue section.

This procedure is also be used for electron microscopy where the fluorophore-tyramide component is replaced by a gold nanoparticle-tyramide conjugate.

Example B

Treat the tissue section with 0.3% $H_2O_2$ in water for 30 minutes to quench endogenous peroxidase activity. Wash the section for 5 minutes with PBS, remove the buffer, and repeat the washing two additional times. The tissue section is then incubated with norbornene or trans-cyclooctene labeled primary antibody (as prepared in the example above) in PBS buffer for 30 minutes. Unbound and non-specifically bound antibody is removed by washing with PBS 3 times for 5 minutes each. After washing, the tissue section is incubated with HRP-tetrazine (as prepared in the example above) in PBS buffer for 30 minutes to conjugate the primary antibody to the HRP-tetrazine via the inverse electron demand Diels-Alder coupling reaction. The tissue section is then washed 3 times for 5 minutes each to remove unconjugated HRP-tetrazine. The tissue section is incubated with dilute $H_2O_2$ (typically 0.5 to 10 µM) and the appropriate tyramide conjugated fluorophore substrate such as, but not limited to, fluorescein tyramide, tetramethylrhodamine tyramide, or Cy5 tyramide. After incubation for the desired time, the procedure is completed by washing with water or PBS 3 times for 5 minutes each to remove any excess fluorophore-tyramide and mounting of the tissue section.

This procedure could also be used for electron microscopy where the fluorophore-tyramide component is replaced by a gold nanoparticle-tyramide conjugate.

Example C

Treat the tissue section with 0.3% $H_2O_2$ in water for 30 minutes to quench endogenous peroxidase activity. Wash the section for 5 minutes with PBS, remove the buffer, and repeat the washing two additional times. The tissue section is then incubated with unlabeled primary antibody in PBS buffer for 30 minutes. Unbound and non-specifically bound antibody is removed by washing with PBS 3 times for 5 minutes each. After washing, the tissue section is incubated with 4% blocking serum in PBS for 30 minutes using serum from the species in which the secondary antibody is made. The diluted serum solution is decanted and the tissue section is washed 3 times for 5 minutes each with PBS. Then the tissue section is incubated with HRP modified secondary antibody for 30 minutes. The tissue section is then washed 3 times for 5 minutes each with PBS to remove unbound and non-specifically bound HRP secondary antibody. The tissue section is incubated with dilute $H_2O_2$ (typically 0.5 to 10 µM) and tetrazine-tyramide or dienophile-tyramide constructs (prepared by coupling of the appropriate N-hydroxysuccinimidyl ester modified tetrazine or dienophile with tyramine) such as 5-(4-(1,2,4,5-tetrazin-3-yl)benzylamino)-5-oxopentanoic acid-tyramide. This results in deposition of tetrazine functionality on the tissue section immediately adjacent to the HRP antibody constructs via cross-linking of the tyramide to surface proteins in the tissue section. The tissue section is then treated with a fluorophore-dienophile conjugate (prepared by reaction of the N-hydroxysuccinimidyl ester of ((1S,2S,4S)-bicyclo[2.2.1]hept-5-en-2-yl acetic acid) or any trans-cyclooctene analog with the desired amine modified fluorophore, such as, but not limited to fluorescein, tetramethylrhodamine, or Cy5). After incubation for the desired time, the procedure is completed by washing with water or PBS 3 times for 5 minutes each to remove any excess fluorophore-dienophile and mounting of the tissue section.

This procedure is also used for electron microscopy where the fluorophore-dienophile component is replaced by a gold nanoparticle-dienophile conjugate.

Example 27

Western Blotting

Example A

Briefly, after running the protein sample on an SDS-PAGE gel and then transferring the protein to a membrane via standard procedures, the membrane is incubated blocking buffer for 30 minutes. The appropriate dilution of the primary antibody, previously modified with trans-cyclooctene (prepared as described in example 20), is then added to the solution, which is able to bind to its specific protein on the membrane. The membrane is incubated in this solution until a sufficient level of antibody binding is obtained. After washing the membrane three times with PBS or water to remove unbound antibody, a tetrazine-fluorophore conjugate (prepared as described in examples 1 and 2), which undergoes inverse electron demand Diels-Alder cycloaddition to the trans-cyclooctene modified primary antibody, is incubated with the membrane for the appropriate time. After washing three times with PBS or water, the fluorescently tagged proteins on the membrane may be visualized by standard fluorescence methodologies.

Example B

Briefly, after running the protein sample on an SDS-PAGE gel and then transferring the protein to a membrane via standard procedures, the membrane is incubated with blocking buffer for 30 minutes to block non-specific sites on the membrane. The appropriate dilution of the primary antibody, previously modified with trans-cyclooctene (prepared as described in example 20), is then added to the solution, which is able to bind to its specific protein on the membrane. The membrane is incubated in this solution until a sufficient level of antibody binding is obtained. After washing the membrane three times with PBS or water (for 5-15 minutes each) to remove unbound antibody, a tetrazine-HRP conjugate (prepared as described in example 19), which undergoes inverse electron demand Diels-Alder cycloaddition to the trans-cyclooctene modified primary antibody, is incubated with the membrane for the appropriate time. After washing three times with PBS or water (for 5-15 minutes each), the membrane is incubated with $H_2O_2$ (typically 0.5 to 10 µM) and the appropriate tyramide conjugated fluorophore substrate such as, but not limited to, fluorescein tyramide, tetramethylrhodamine tyramide, or Cy5 tyramide. After incubation for the desired time, the membrane is washed with PBS or water 3 times (for 5-15 minutes each) to remove non-coupled fluorophore-tyramide and the membrane is imaged by standard fluorescence procedures. Alternatively, instead of incubation with $H_2O_2$ (typically 0.5 to 10 µM) and the appropriate tyramide conjugated fluorophore, the fluorophore can be replaced with a chemiluminescent substrate such as, but not limited to luminol After addition of the $H_2O_2$/luminol solution to the membrane, in 1-5 minutes, the membrane may be imaged without washing by exposure of the membrane to X-ray film or with an appropriate digital camera system.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound selected from the group consisting of

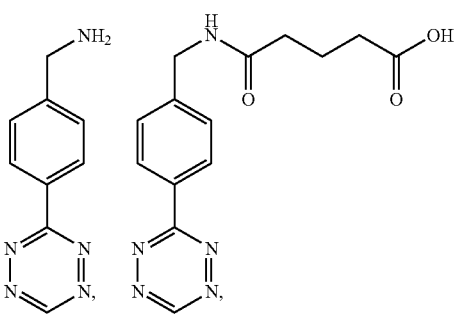

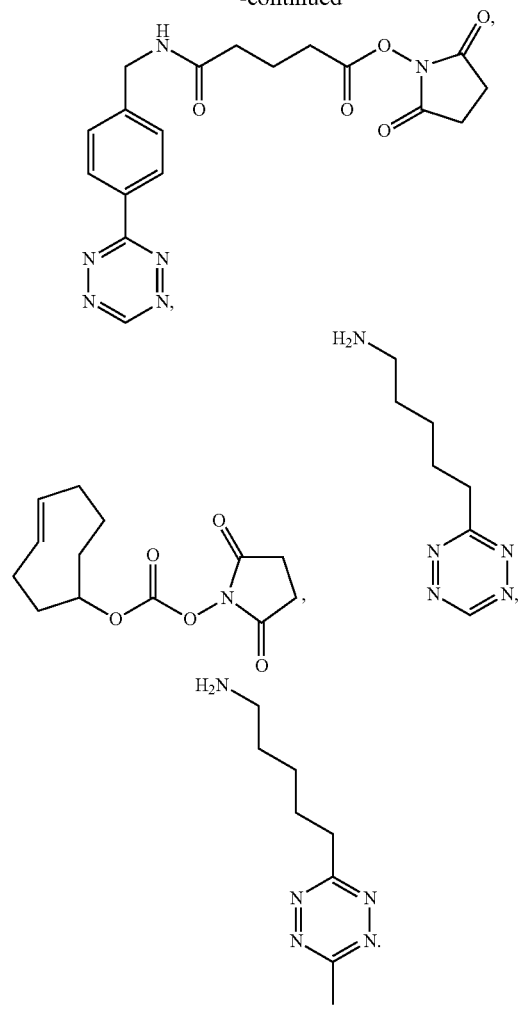
2. A composition comprising a compound selected from the group consisting of
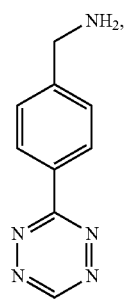
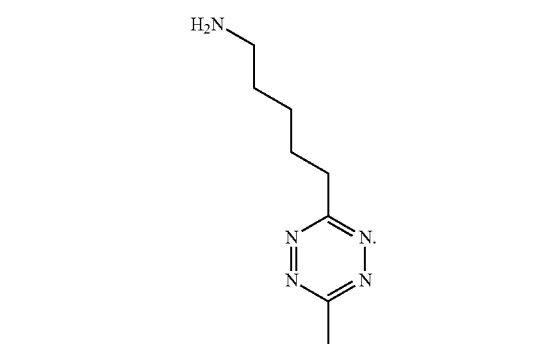
* * * * *